US012564828B2

(12) United States Patent
Nishiyama et al.

(10) Patent No.: US 12,564,828 B2
(45) Date of Patent: Mar. 3, 2026

(54) CATALYST AND METHOD FOR PRODUCING DIENE COMPOUND

(71) Applicant: SEKISUI CHEMICAL CO., LTD., Osaka (JP)

(72) Inventors: Haruka Nishiyama, Tsukuba (JP); Noritoshi Yagihashi, Tsukuba (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 866 days.

(21) Appl. No.: 17/621,848

(22) PCT Filed: Jun. 24, 2020

(86) PCT No.: PCT/JP2020/024894
§ 371 (c)(1),
(2) Date: Dec. 22, 2021

(87) PCT Pub. No.: WO2020/262486
PCT Pub. Date: Dec. 30, 2020

(65) Prior Publication Data
US 2022/0288562 A1      Sep. 15, 2022

(30) Foreign Application Priority Data

Jun. 25, 2019    (JP) ................................. 2019-117320
Jun. 25, 2019    (JP) ................................. 2019-117332
Jun. 25, 2019    (JP) ................................. 2019-117343

(51) Int. Cl.
| | |
|---|---|
| *B01J 21/16* | (2006.01) |
| *B01J 35/23* | (2024.01) |
| *B01J 35/61* | (2024.01) |
| *B01J 35/64* | (2024.01) |
| *B01J 35/70* | (2024.01) |
| *C01B 33/20* | (2006.01) |
| *C07C 1/20* | (2006.01) |
| *C08F 36/06* | (2006.01) |

(52) U.S. Cl.
CPC ............... *B01J 21/16* (2013.01); *B01J 35/23* (2024.01); *B01J 35/617* (2024.01); *B01J 35/618* (2024.01); *B01J 35/647* (2024.01); *B01J 35/70* (2024.01); *C01B 33/20* (2013.01); *C07C 1/20* (2013.01); *C08F 36/06* (2013.01); *B01J 2235/00* (2024.01); *B01J 2235/15* (2024.01); *B01J 2235/30* (2024.01); *C01P 2002/72* (2013.01); *C01P 2002/74* (2013.01); *C01P 2006/12* (2013.01); *C01P 2006/16* (2013.01); *C07C 2521/16* (2013.01)

(58) Field of Classification Search
CPC ...... B01J 35/617; B01J 35/647; B01J 21/066; B01J 29/041; C07C 1/20; C07C 2521/06; C08F 36/06; C01P 2002/72; C01P 2002/74; C01P 2006/16; C07F 7/00
See application file for complete search history.

(56) References Cited

U.S. PATENT DOCUMENTS

| | | | |
|---|---|---|---|
| 11,642,657 B2 * | 5/2023 | Klotz Rabello | ......... B01J 23/08 |
| 2015/0266988 A1 * | 9/2015 | Kojima | ................... C12P 5/026 |
| 2018/0147560 A1 * | 5/2018 | Hsu | ........................... B01J 37/04 |
| 2018/0200694 A1 | 7/2018 | Cadran et al. | |
| 2021/0170364 A1 | 6/2021 | Nishiyama et al. | |
| 2023/0158475 A1 * | 5/2023 | Takizawa | ................. B01J 21/08 |

FOREIGN PATENT DOCUMENTS

| | | | | |
|---|---|---|---|---|
| CN | 103483130 | 1/2014 | | |
| EP | 3738670 | 11/2020 | | |
| JP | 2006-272217 | 10/2006 | | |
| KR | 10-2014-0050531 | 4/2014 | | |
| WO | 2014/199349 | 12/2014 | | |
| WO | WO-2017009105 A2 * | 1/2017 | .............. | B01J 21/08 |
| WO | 2019/131890 | 7/2019 | | |
| WO | 2019/139071 | 7/2019 | | |
| WO | WO-2019131890 A1 * | 7/2019 | .............. | C07C 1/20 |
| WO | WO-2020158751 A1 * | 8/2020 | .............. | C07C 1/20 |

OTHER PUBLICATIONS

Pooja Gaval, Catalysts for butadiene synthesis by Ostromyslensky process developed by surface organometallic chemistry, PhD Thesis, University of Lyon, France (Year: 2018).*
Estevenon et al. Soft Hydrothermal Synthesis of Hafnon, HfSiO, Crystal Growth and Design, 20(3) pp. 1820-1828 (Year: 2020).*
Processing and crystallographic structure of non-equilibrium Si-doped HfO2, Journal of Applied Physics, 117, 244103 (Year: 2015).*
Udayakumar et al., "Synthesis of Hf/SBA-15 Lewis acid catalyst for converting glycerol to value-added chemicals", Journal of Porous Materials, Nov. 25, 2016, vol. 24, No. 4, pp. 979-990.
Osuga et al., "Development of Hf-containing SBA-15 catalysts with highly dispersed active sites for 1,3-butadiene production from ethanol and acetaldehyde", Microporous and Mesoporous Materials, Dec. 1, 2022, vol. 346, pp. 1-7.
International Search Report (ISR) issued Sep. 8, 2020 in International (PCT) Application No. PCT/JP2020/024894.
Anne Galarneau et al., "Microporosity and connections between pores in SBA-15 mesostructured silicas as a function of the temperature of synthesis", New. J. Chem., vol. 27, pp. 73-79, Nov. 28, 2002, cited in ISR.

* cited by examiner

*Primary Examiner* — Katarzyna I Kolb
(74) *Attorney, Agent, or Firm* — Wenderoth, Lind & Ponack, L.L.P.

(57) ABSTRACT

A catalyst includes at least one element X selected from the group consisting of Groups 3 to 6 of the Periodic Table, and at least one element Z selected from the group consisting of Group 14 elements. At least one diffraction peak is observed in a low angle range of $\theta=6°$ or less in an X-ray diffraction profile observed using X-ray diffraction. The at least one diffraction peak has a ratio (I/H) of a peak intensity I to a half width at half maximum H of the diffraction peak of 5000 or more.

10 Claims, 2 Drawing Sheets

CATALYST AND METHOD FOR PRODUCING DIENE COMPOUND

TECHNICAL FIELD

The present invention relates to a catalyst and a method for producing a diene compound using the catalyst.

BACKGROUND ART

Butadienes such as 1,3-butadiene, which is a representative example of a diene compound, are used as a raw material of styrene-butadiene rubber (SBR) and the like. Conventionally, butadiene has been purified from the C4 fraction. The C4 fraction is a fraction produced as a by-product during naphtha cracking for which producing ethylene from petroleum. However, with the increase in shale gas use, the amount of oil that is used has decreased. As a result, the amount of butadiene obtained by naphtha cracking of petroleum is also decreasing. For this reason, alternative methods for producing diene compounds such as 1,3-butadiene are required.

For example, Patent Literature 1 describes an invention relating to a metal-impregnated silica catalyst for selectively converting ethanol into butadiene. More specifically, Patent Literature 1 describes a catalyst for butadiene synthesis which includes Hf and two or more catalytically active metals M1 and M2. These two or more catalytically active metals M1 and M2 are selected from the group consisting of Zr, Zn, Cu, and combinations thereof, and M1 and M2 are different from each other.

Patent Literature 1 describes a method for synthesizing a butadiene including: (i) providing a gas flow G-1 including ethanol and optionally acetaldehyde, and (ii) contacting the gas flow G-1 with the catalyst for butadiene synthesis to obtain a gas flow G-2 including butadiene.

According to the described method for synthesizing butadiene, the butadiene selectivity is at least 10%.

CITATION LIST

Patent Literature

PTL1: WO 2014/199349 A1

SUMMARY OF INVENTION

Technical Problem

Since the catalyst for butadiene synthesis described in Patent Literature 1 is a supported catalyst in which a catalytically active metal is supported by silica or the like as a carrier, the dispersing ability of the catalytically active metal on the carrier surface determines the selectivity to the diene compound such as butadiene. When the selectivity of the diene compound (e.g., butadiene), which is the target product, is low, there is a detrimental effect in that separation and purification of the diene compound in subsequent steps becomes complicated.

Accordingly, it is an object of a first aspect of the present invention to provide a catalyst capable of selectively producing a diene compound, particularly butadiene, at a high yield.

Further, depending on the supported state of the catalytically active metal, not only is a diene compound produced, but a polymer may also be produced due to an excessive progression of reaction. If such an excessive progression of reaction progresses too much, not only does the diene compound selectivity decrease, but there is a detrimental effect in that the polymer poisons the active metal and promotes a deterioration in activity, and subsequent separation and purification becomes complicated.

Accordingly, it is an object of a second aspect of the present invention to provide a catalyst which is capable of producing a diene compound, particularly butadiene, at a high yield and which suppresses a deterioration in activity.

Further, it is an object of a third aspect of the present invention to provide a catalyst which suppresses an excessive progression of reaction to a polymer and which is capable of producing a diene compound, particularly butadiene, at a high yield.

Solution to Problem

The present inventors have conducted intensive research to solve the above-described problems relating to the first aspect of the present invention. As a result, in a first aspect of the present invention, it was found that the above-described problems relating to the first aspect of the present invention are solved by a catalyst including predetermined elements and having a diffraction peak in a low angle range of $\theta=6°$ or less in an X-ray diffraction profile, whereby the present invention was completed. That is, the invention according to the first aspect of the present invention has the following modes.

[1-1] A catalyst comprising:

at least one element X selected from the group consisting of Groups 3 to 6 of the Periodic Table; and at least one element Z selected from the group consisting of Group 14 elements, wherein at least one diffraction peak is observed in a low angle range of $\theta=6°$ or less in an X-ray diffraction profile observed using X-ray diffraction, and the at least one diffraction peak has a ratio (I/H) of a peak intensity I to a half width at half maximum H of the diffraction peak of 5000 or more.

[1-2] The catalyst according to [1-1], wherein a molar content $(X/(X+Z)\times100)$ of the element X with respect to the total amount (mole) of the element X and the element Z is 0.5 to 6 mol %.

[1-3] The catalyst according to [1-1] or [1-2], wherein the element X is Hf and the element Z is Si.

[1-4] The catalyst according to any of [1-1] to [1-3], wherein the catalyst is a diene compound synthesis catalyst for synthesizing a diene compound from a raw material including an alcohol.

[1-5] The catalyst according to [1-4], wherein the raw material includes ethanol and/or acetaldehyde.

[1-6] The catalyst according to any of [1-1] to [1-5], wherein a BET specific surface area is 700 to 1200 $m^2/g$ and an average pore size is 2 to 20 nm.

[1-7] The catalyst according to any of [1-1] to [1-6], wherein at least one diffraction peak having a half width at half maximum of 1° or more is observed in a high angle range of $\theta=10°$ to 40° in an X-ray diffraction profile observed using X-ray diffraction.

[1-8] A method for producing a diene compound, comprising contacting a raw material including an alcohol with the catalyst according to any of [1-1] to [1-7] to produce the diene compound.

[1-9] A method for producing a polymer, comprising producing the polymer by using at least a portion of the diene compound produced by the method for producing a diene compound according to [1-8] as a polymer raw material.

[1-10] A method for producing a polymer formed article, comprising forming the polymer produced by the method for producing a polymer according to [1-9].

Further, the present inventors have conducted intensive research to solve the above-described problems relating to the second aspect of the present invention. As a result, in a second aspect of the present invention, it was found that the above-described problems relating to the second aspect of the present invention are solved by a catalyst including predetermined elements and having a BET specific surface area and an average pore size set to be in specific ranges, whereby the present invention was completed. That is, the invention according to the second aspect of the present invention has the following modes.

[2-1] A catalyst comprising:
  at least one element X selected from the group consisting of Groups 3 to 6 of the Periodic Table; and
  at least one element Z selected from the group consisting of Group 14 elements, wherein a BET specific surface area is 700 to 1200 m/g and an average pore size is 2 to 20 nm.

[2-2] The catalyst according to [2-1], wherein a molar content $(X/(X+Z)\times100)$ of the element X with respect to the total amount (mole) of the element X and the element Z is 0.5 to 6 mol %.

[2-3] The catalyst according to [2-1] or [2-2], wherein the element X is Hf and the element Z is Si.

[2-4] The catalyst according to any of [2-1] to [2-3], wherein the catalyst is a diene compound synthesis catalyst for synthesizing a diene compound from a raw material including an alcohol.

[2-5] The catalyst according to [2-4], wherein the raw material includes ethanol and/or acetaldehyde.

[2-6] A method for producing a diene compound, comprising contacting a raw material including an alcohol with the catalyst according to any of [2-1] to [2-5] to produce the diene compound.

[2-7] A method for producing a polymer, comprising producing the polymer by using at least a portion of the diene compound produced by the method for producing a diene compound according to [2-6] as a polymer raw material.

[2-8] A method for producing a polymer formed article, comprising forming the polymer produced by the method for producing a polymer according to [2-7].

The present inventors have conducted intensive research to solve the above-described problems relating to the third aspect of the present invention. As a result, in a first aspect of the present invention, it was found that the above-described problems relating to the first aspect of the present invention are solved by a catalyst having a specific complex oxide structure including predetermined elements, whereby the present invention was completed. That is, the invention according to the first aspect of the present invention has the following modes.

[3-1] A catalyst comprising:
  at least one element X selected from the group consisting of Groups 3 to 6 of the Periodic Table; and
  at least one element Z selected from the group consisting of Group 14 elements, wherein
  at least one diffraction peak having a half width at half maximum of 1° or more is observed in a high angle range of θ=10° to 40° in an X-ray diffraction profile observed using X-ray diffraction.

[3-2] The catalyst according to [3-1], wherein of the diffraction peaks, a ratio (I/H) of the peak intensity I of the largest diffraction peak with the maximum diffraction intensity to the half width at half maximum H of that maximum diffraction peak is 1000 to 3000.

[3-3] The catalyst according to [3-1] or [3-2], wherein a diffraction peak due to a single oxide of the element X is not observed in a diffraction angle range of θ=10° to 40° in the X-ray diffraction profile.

[3-4] The catalyst according to any of [3-1] to [3-3], wherein a molar content $(X/(X+Z)\times100)$ of the element X with respect to the total amount (mole) of the element X and the element Z is 0.5 to 6 mol %.

[3-5] The catalyst according to any of [3-1] to [3-4], wherein at least one diffraction peak having a half width at half maximum of 1° or more is observed in a range of θ=10° to 40°.

[3-6] The catalyst according to any of [3-1] to [3-5], wherein the half width at half maximum is 6° to 12°.

[3-7] The catalyst according to any of [3-1] to [3-6], wherein the element X is Hf and the element Z is Si.

[3-8] The catalyst according to any of [3-1] to [3-7], wherein the catalyst is a diene compound synthesis catalyst for synthesizing a diene compound from a raw material including an alcohol.

[3-9] The catalyst according to [3-8], wherein the raw material includes ethanol and/or acetaldehyde.

[3-10] A method for producing a diene compound, comprising contacting a raw material including an alcohol with the catalyst according to any of [3-1] to [3-9] to produce the diene compound.

[3-11] A method for producing a polymer, comprising producing the polymer by using at least a portion of the diene compound produced by the method for producing a diene compound according to [3-10] as a polymer raw material.

[3-12] A method for producing a polymer formed article, comprising forming the polymer produced by the method for producing a polymer according to [3-11].

Advantageous Effects of Invention

According to the invention according to the first aspect of the present invention, a catalyst capable of selectively producing a diene compound, particularly butadiene, at a high yield can be provided.

According to the invention according to the second aspect of the present invention, a catalyst which is capable of producing a diene compound, particularly butadiene, at a high yield and which suppresses a deterioration in activity, can be provided.

According to the invention according to the third aspect of the present invention, a catalyst which suppresses an excessive progression of reaction to a polymer and which is capable of producing a diene compound, particularly butadiene, at a high yield can be provided.

DESCRIPTION OF EMBODIMENTS

Figure 1:
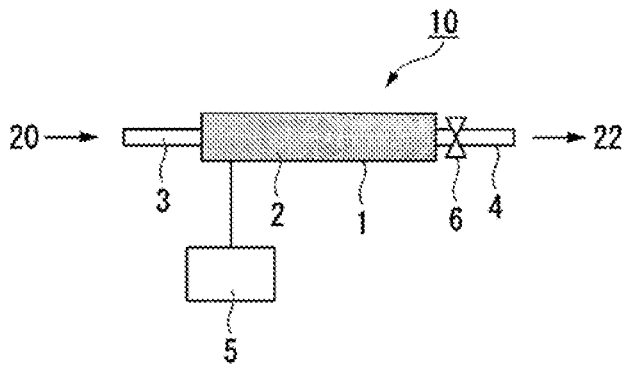
FIG. 1 is a schematic diagram illustrating a diene compound production apparatus according to one embodiment of the present invention.

Hereinafter, a mode of carrying out each of the inventions according to the first to third aspects of the present invention will be described in detail. However, the following description is an example of the embodiments of the present invention. The present invention is not limited to this subject matter, and can be carried out by modifying within the gist thereof.

In addition, the invention according to the first aspect of the present invention is referred to as the first invention, the invention according to the second aspect of the present invention is referred to as the second invention, and the invention according to the third aspect of the present invention is referred to as the third invention.

<<First Invention>>

<Catalyst>

The catalyst according to the present embodiment includes at least one element X selected from the group consisting of Groups 3 to 6 of the Periodic Table and at least one element Z selected from the group consisting of Group 14 elements. By containing the element X, the raw material can be converted into a diene compound. Further, by including the element Z, the contact area between the raw material and the catalyst can be increased.

The catalyst according to the present embodiment has at least one diffraction peak observed in a low angle range of $\theta=6°$ or less in an X-ray diffraction profile observed using X-ray diffraction, preferably in the range of $\theta=0.1°$ to 6°, and more preferably in the range of $\theta=0.1°$ to 1°. This at least one diffraction peak has a ratio (I/H) of a peak intensity I to a half width at half maximum H of the diffraction peak of 5000 or more, preferably 6000 or more, and more preferably 7000 or more.

This diffraction peak is due to the fact that the catalyst including the elements X and Y has mesopores with a specific regular arrangement. It is conjectured that the presence of this regular arrangement makes it easier for the raw material ethanol and the intermediate product crotonaldehyde to enter into the mesopores, for example, increasing the frequency of collisions between them, thereby improving reactivity so that butadiene is selectively produced. On the other hand, if the diffraction peak is not observed, this means that mesopores with a regular arrangement are not present in the catalyst. Therefore, it is conjectured that the reaction stops at acetaldehyde, which is an intermediate product. The conditions of the X-ray diffraction are as described in the examples.

The catalyst according to the present embodiment has an average pore size of 2 to 50 nm, preferably 2 to 30 nm, more preferably 2 to 20 nM, and further preferably 2 to 15 nm. Here, the "average pore size" of the catalyst is a value measured by the following method. That is, the average pore size is calculated from the total pore volume (sum of the pore volume of the catalyst) and the BET specific surface area.

Specifically, the average pore size can be calculated by assuming that the pores have a cylindrical shape (BJH method). The average pore size can then be calculated by $4V1/A1$, in which a BET specific surface area A1 is taken to be the surface area of the side of the cylinder and a total pore volume V1 is taken to be the volume of the cylinder.

The total pore volume of the catalyst is preferably 0.1 to 10.0 mug, more preferably 0.1 to 5.0 mL/g, and further preferably 0.1 to 2.0 mL/g. The total pore volume is preferably 0.1 mL/g or more because the diffusibility of the alcohol is improved, and the raw material conversion rate and diene compound selectivity are further increased. On the other hand, the total pore volume is preferably 10.0 mL/g or less because the contact area between the alcohol and the catalyst increases, and the raw material conversion rate and diene compound selectivity are further increased. As used herein, the "total pore volume" of the catalyst is a value measured by gas adsorption. At such time, gas adsorption refers to a method in which nitrogen gas is used as an adsorption gas, nitrogen molecules are adsorbed on the surface of the synthesis catalyst, and the pore distribution is measured from the condensation of the molecules.

The specific surface area of the catalyst is preferably 100 to 10000 $m^2/g$, more preferably 200 to 5000 $m^2/g$, further preferably 200 to 1500 $m^2/g$, and particularly preferably 700 to 1200 $m^2/g$.

The specific surface area is preferably 100 $m^2/g$ or more because there are sufficient numbers of active points on the catalyst surface, so that the raw material conversion rate and diene compound selectivity are further increased. As a result, the raw material conversion rate increases even if the content of the raw material is a high concentration with respect to 100% by volume (gas equivalent) of the raw material, and for example, a high raw material conversion rate is exhibited even at 100% by volume. On the other hand, the specific surface area is preferably 10000 $m^2/g$ or less because the contact area between the raw material and the catalyst increases, and the raw material conversion rate and diene compound selectivity are further increased.

As used herein, "specific surface area" means the BET specific surface area measured by BET gas adsorption with nitrogen as the adsorption gas.

The product of the total pore volume and the specific surface area of the catalyst is preferably 10 to 100000 $mL·m^2/g^2$, more preferably 20 to 25000 $mL·m^2/g^2$, and further preferably 20 to 2000 $mL·m^2/g^2$. The product is preferably 10 $mL·m^2/g^2$ or more because there are sufficient numbers of active points on the catalyst surface and the diffusibility of the raw material including an alcohol is improved, so that the raw material conversion rate and diene compound selectivity are further increased. On the other hand, the product is preferably 100000 $mL·m^2/g^2$ or less because the contact area between the raw material and the catalyst tends to be sufficient, and the raw material conversion rate and diene compound selectivity are further increased.

The mesopore volume ratio (total mesopore volume/total pore volume×100) of the catalyst is preferably 50% or more, more preferably 50 to 100%, further preferably 80 to 100%, and particularly preferably 90 to 100%. The mesopore volume ratio is preferably 50% or more because sufficient mesopores are present in the catalyst, and the diffusibility of the raw material including an alcohol is improved, so that the raw material conversion rate and diene compound selectivity are further increased.

The ratio of the mesopore pore volume ratio can be controlled based on the usage ratio of the raw material (compound including X, compound including Z, etc.) in the production method described later, firing temperature in the firing step, and the like.

The shape of the mesopores of the catalyst and whether the pore wall forming the mesopores has a crystal structure can be confirmed by observing the diffraction peaks by X-ray diffraction. Further, the shape and regularity of the mesopores can be confirmed by observing the synthesis catalyst with a transmission electron microscope (TEM).

Further, it is preferable that at least one diffraction peak having a half width at half maximum of 1° or more is observed in a high angle range of $\theta=10°$ to 40°, and preferably in the range of $\theta=20°$ to 25°, in an X-ray diffraction profile of the catalyst observed using X-ray diffraction. This diffraction peak is due to the complex oxide including the element X and the element Y. The presence of this complex oxide suppresses an excessive progression of reaction to a polymer that tends to progress on the aggregate of the single oxide of the element X, thereby enabling the diene compound to be selectively obtained in a high yield.

As used herein, "complex oxide" refers to an oxide in which two or more elements (metals, etc.) including the element X and the element Y coexist. In the case of a supported catalyst in which the element X is supported on the surface of a carrier including element Y, a diffraction peak due to the complex oxide as described above is not obtained.

Further, the "polymer" produced by an excessive progression of reaction refers to an unsaturated carbide or saturated carbide having 5 or more carbon atoms, such as pentadiene, pentene, pentane, hexadiene, hexatriene, hexene, and hexane, and the like.

It is preferable that a diffraction peak due to a single oxide of the element X is not observed in the high angle range of $\theta=10°$ to $40°$. When such a diffraction peak is not observed, this means that most of the element X is a component of the complex oxide, and the conversion function of the element X into a diene compound can be sufficiently exhibited. Further, the excessive progression of reaction of the element X to a polymer that tends to progress on the aggregate of the single oxide (for example, hafnium oxide etc.) is suppressed.

Here, the fact that no diffraction peak due to the single oxide of the element X is observed means that the ratio (I/H) of the peak intensity I of the diffraction peak to the half width at half maximum H of the diffraction peak is 900 or less.

Crystallinity increases as the half width at half maximum of the diffraction peak becomes smaller, but in the present embodiment, the half width at half maximum is preferably $6°$ to $12°$, and more preferably $7°$ to $11°$.

Since the half width at half maximum is $6°$ to $12°$, there is a gap between each of the elements constituting complex oxide, and hence it is conjectured that the reaction to the diene compound tends to progress selectively.

Of the diffraction peaks, the ratio (I/H) of the peak intensity I of the largest diffraction peak with the maximum diffraction intensity to the half width at half maximum H of that maximum diffraction peak is preferably 1000 to 3000, and more preferably 1500 to 2200.

Since the ratio (I/H) is 1000 to 3000, the reaction to butadiene tends to selectively progress.

Here, examples of the element X include Group 3 elements such as scandium (Sc), yttrium (Y), lanthanum (La), and cerium (Ce); Group 4 elements such as titanium (Ti), zirconium (Zr), and hafnium (Hf); Group 5 elements such as vanadium (V), niobium (Nb), and tantalum (Ta); and Group 6 elements such as chromium (Cr), molybdenum (Mo), and tungsten (W). Of these, the element X is preferably a Group 3 element, a Group 4 element, or a Group 5 element, more preferably a Group 4 element or a Group 5 element, and further preferably a Group 4 element.

Further, according to another embodiment, the element X is preferably a Period 5 element, a Period 6 element, or a Period 7 element, and more preferably a Period 5 element or a Period 6 element. Specifically, the element X is preferably ytrium (Y), lanthanum (La), cerium (Ce), titanium (Ti), zirconium (Zr), hafnium (Hf), vanadium (V), niobium (Nb), tantalum (Ta), molybdenum (Mo), or tungsten (W), more preferably yttrium (Y), lanthanum (La), cerium (Ce), titanium (Ti), zirconium (Zr), hafnium (Hf), niobium (Nb), or tantalum (Ta), further preferably zirconium (Zr), hafnium (Hf), niobium (Nb), or tantalum (Ta), particularly preferably zirconium (Zr), hafnium (Hf), or niobium (Nb), very preferably is niobium (Nb) or hafnium (Hf), and most preferably hafnium (Hf).

The element X may include one type alone or may include two or more types in combination.

Examples of the element Z include carbon (C), silicon (Si), germanium (Ge), and tin (Sn).

Of these, the element Z is preferably carbon (C) or silicon (Si), and more preferably silicon (Si).

One type of the element Z may be included, or two or more types may be included in combination.

Further, a particularly preferable combination is Hf as the element X and Si as the element Z.

The molar content ($X/(X+Z)\times100$) of the element X with respect to the total amount (moles) of the element X and the element Z in the catalyst is preferably 0.1 to 20 mol %, more preferably 0.5 to 15 mol %, further preferably 0.5 to 6 mol %, and particularly preferably 0.7 to 4 mol %.

When two or more of the element X are included in combination and two or more of the element Z are included in combination, the molar content is calculated based on the sum of those two or more types of the element X and two or more types of the element Z.

In one preferred embodiment, the catalyst preferably satisfies the following general formula 1.

$$X_{a1}Si_{b1}O_{\delta1} \qquad\qquad \text{formula 1}$$

In formula 1, X represents the element X.

a1 is the molar ratio of the element X, and when the sum of a1 and b1 is 100 mol %, a1 is preferably 0.1 to 20 mol %, more preferably 0.5 to 15 mol %, further preferably 0.5 to 6 mol %, and particularly preferably 0.7 to 4 mol %.

b1 is the molar ratio of Si, and when the sum of a1 and b1 is 100 mol %, b1 is preferably 80 to 99.9 mol %, more preferably 85 to 99.5 mol %, further preferably 94 to 99.5 mol %, and particularly preferably 94 to 99.3 mol %.

$\delta1$ represents the number required to satisfy the charge neutral condition. Specifically, $\delta1$ is defined by the elements X and Si constituting the catalyst, and a1 and b1. For example, $\delta1$ is preferably 100 to 2000, more preferably 100 to 1000, and further preferably 100 to 400.

The fact that the molar content of the element X and the catalyst are represented by general formula 1 can be confirmed by, for example, light emission spectroscopy or X-ray fluorescence measurement.

To the extent that the effects of the present invention are not impaired, the catalyst of the present embodiment may include elements other than the element X and the element Z, such as the element zinc (Zn), as constituent elements of the complex oxide.

In addition, when elements other than the element X and the element Z are included as the constituent elements of complex oxide (hereinafter, such elements are also referred to as "other elements"), regarding the molar ratio of the element X, the element Z, and the other elements, it is preferable that the molar ratio of the element Z is reduced by the molar ratio of the other elements, as described above. In other words, the molar ratio of the element X is preferably the same molar ratio regardless of whether or not other elements are included. This is the same even when two or more other elements are included.

The above-described catalyst is preferably a catalyst for synthesizing a diene compound that synthesizes a diene compound from a raw material including an alcohol. In such a case, as described later, it is preferable to include ethanol and/or an acetaldehyde as the alcohol, and it is more preferable to include ethanol. Further, as described later, it is preferable that the diene compound is 1,3-butadiene.

<Method for Producing Catalyst>

The catalyst according to the present embodiment is produced by carrying out a solid colloid preparation step and a firing step. Hereinafter, each step will be described.

[Solid Colloid Preparation Step]

The solid colloid preparation step is s step of obtaining a solid colloid by distilling off at least a part of the solvent in a raw material solution which includes a compound including at least one element X selected from the group consisting of Groups 3 to 6 of the Periodic Table, a compound including at least one element Z selected from the group consisting of Group 14 elements, a surfactant, and a solvent including water.

(Raw Material Solution)

The raw material solution includes a compound including at least one element X selected from the group consisting of Groups 3 to 6 of the Periodic Table, a compound including at least one element Z selected from the group consisting of Group 14 elements, a surfactant, and a solvent including water. The raw material solution may further include a compound including another element (e.g., a compound including zinc), an acidic solution, a basic solution, and the like.

In the catalyst according to the present embodiment, in order to obtain a catalyst that has at least one diffraction peak observed in a low angle range of $\theta=6°$ or less in an X-ray diffraction profile and that has a ratio (I/H) of a peak intensity I of the at least one diffraction peak to a half width at half maximum H of the diffraction peak of 5000 or more, it is preferable that the raw material solution is prepared as follows.

(1) First, water and an acidic solution or a basic solution are added to a predetermined amount of surfactant, and the surfactant is dissolved by stirring at a predetermined speed (e.g., about 50 to 200 rpm) under ordinary temperature and pressure conditions.

It is preferable to add the acidic solution or basic solution so that the raw material solution to be prepared has an acidity or basicity of 0.001 mol/L to 10 mol/L (preferably 0.01 to 5 mol/L). The acidic solution or basic solution promotes the hydrolysis of precursors such as the compound including the element X and the compound including the element Z. By being in the above range, the hydrolysis rate of the metal precursors is not too high, and as a result, aggregation between single metal oxides is prevented, and the complex oxide can be efficiently obtained.

(2) The compound including the element X is added at a predetermined rate while stirring the aqueous solution in which the surfactant is dissolved at a predetermined speed under ordinary temperature and pressure conditions.

The stirring speed when stirring at the predetermined speed is preferably 10 to 2000 rpm, more preferably 10 to 1000 rpm, and further preferably 10 to 500 rpm. By setting the stirring speed to be within the above range, aggregation is prevented between single metal oxides, and the complex oxide can be efficiently obtained.

Further, the addition rate when adding the compound including the element X at a predetermined rate is preferably 0.1 to 100 mg/min, more preferably 0.1 to 50 mg/min, and further preferably 0.1 to 20 mg/min. In the above range, while being a practical addition rate, aggregation between single metal oxides is prevented, and a complex oxide can be efficiently obtained.

In addition, the concentration of the compound including the element X in the raw material solution to be prepared is preferably in the range of 0.001 to 1000 g/L, and more preferably in the range of 0.01 to 100 g/L. In the above range, while having good handling in the subsequent steps, aggregation between single metal oxides is prevented, and a complex oxide can be efficiently obtained.

(3) After confirming that all of the compound including the element X has been dissolved, the compound including the element Z is added at a predetermined rate while stirring at a predetermined rate under ordinary temperature and pressure conditions to prepare a raw material solution.

The predetermined rate when adding the compound including the element Z is preferably 0.01 to 10 g/min, more preferably 0.01 to 5 g/min, and further preferably 0.01 to 1 g/min. By setting the predetermined rate to be no more than the upper limit value of the above range, the hydrolysis reaction rate of the compound including the element Z is prevented from becoming too fast, the reaction progresses more easily around the surfactant, and it is easier to produce mesopores having a regular arrangement. By setting the predetermined rate to be no less than the lower limit value of the above range, it is possible to prevent hydrolysis with moisture in the air during the addition of the compound including the element Z.

The concentration of the compound including the element Z in the raw material solution to be prepared is preferably in the range of 0.001 to 1000 g/L, and more preferably in the range of 0.01 to 100 g/L. By setting the concentration to be no more than the upper limit value of the above range, the hydrolysis reaction rate of the compound including the element Z is prevented from becoming too fast, the reaction tends to progress around the surfactant, and it is easier to produce mesopores having a regular arrangement. By setting the concentration to be no less than the lower limit value of the above range, it is possible to prevent hydrolysis with moisture in the air during the addition of the compound including the element Z.

In addition, the compound including the element Z is added such that a mass ratio to the surfactant (compound including the element Z/surfactant) is preferably 0.01 to 100, and more preferably 0.05 to 50, and further preferably 0.1 to 10. By adding such that the mass ratio is not more than the upper limit value of the above range, the compound including the element Z tends to react the surfactant and is formed more easily. By adding such that the mass ratio is not less than the lower limit value of the above range, it is possible to prevent the formation of oxides (silica etc.) partially including the element Z due to there being too much surfactant, which results in a divided structure, and mesopores having a regular arrangement are formed more easily in the catalyst.

The stirring speed of the raw material solution when adding the compound including the element Z is preferably 10 to 2000 rpm, more preferably 10 to 1000 rpm, and further preferably 10 to 500 rpm. By being in the above range, the hydrolysis of the compound including the element Z is not too early, an interaction with the surfactant occurs so that sufficient mesopores are obtained, and the specific surface area can also be increased.

(4) Then, a suspension is obtained by aging the raw material solution.

The suspension becomes a suspension when the compound including the element X and the compound including the element Z in the above-described raw material solution are hydrolyzed and condensed by water, thereby obtaining solids.

As used herein, "aging" means leaving the raw material solution to stand.

At this time, the aging temperature of the raw material solution is preferably 30 to 200° C., and more preferably 35 to 150° C.

Further, the aging time of the raw material solution is preferably 2 hours to 10 days, and more preferably 10 hours to 5 days.

The aging may be performed in two stages. For example, the first aging may be performed by leaving to stand at 30 to 90° C. for 1 hour to 5 days, and then a second aging may be performed at a higher temperature than the first aging by leaving to stand at 90° C. to 200° C. for 1 hour to 5 days.

Hereinafter, the compound including the element X, the compound including the element Z, the compound including zinc, the surfactant, the solvent, the acidic solution, the basic solution, and the like which are used to produce the raw material solution are described.

Compound Including Element X

Examples of the compound including the element X include, but are not particularly limited to: inorganic salts, such as a chloride, a sulfide, a nitrate, or a carbonate of the element X; organic salts, such as an oxate, an acetylacetonato salt, a dimethyl glyoxime salt, or an ethylenediamine acetate of the element X; chelate compounds of the element X; carbonyl compounds of the element X; cyclopentadienyl compounds of the element X; ammine complexes of the element X; alkoxide compounds of the element X; alkyl compounds of the element X, and the like.

Specifically, examples include titanium chloride ($TiCl_2$, $TiCl_3$, $TiCl_4$), zirconium chloride ($ZrCl_2$), hafnium chloride ($HfCl_4$), niobium chloride ($NbCl_5$), tantalum chloride ($TaCl_5$), vanadium chloride ($VCl_3$) tungsten chloride ($WCl_5$), scandium nitrate ($Sc(NO_3)_3$), yttrium nitrate ($Y(NO_3)_3$), lanthanum nitrate ($La(NO_3)_3$), cerium nitrate ($Ce(NO_3)_3$), and the like.

One type of the above-described compound including the element X may be used alone, or two or more types may be used in combination.

The amount of the compound including the element X that is used is, with respect to the total amount (moles) of the compound including the element X and the compound including the element Z, preferably 0.1 to 20 mol %, more preferably 0.5 to 15 mol %, further preferably 0.5 to 6 mol %, and particularly preferably 0.7 to 4 mol %. In addition, when two or more of the compounds including the element X are included in combination, it is preferable that the sum thereof is included in the above range.

Compound Including Element Z

Examples of the compound including the element Z include, but are not particularly limited to: inorganic salts, such as a chloride, a sulfide, a nitrate, or a carbonate of the element Z; organic salts, such as an oxate, an acetylacetonato salt, a dimethyl glyoxime salt, or an ethylenediamine acetate of the element Z; chelate compounds of the element Z; carbonyl compounds of the element Z; cyclopentadienyl compounds of the element Z; ammine complexes of the element Z; alkoxide compounds of the element Z; alkyl compounds of the element Z, and the like.

Among these, it is preferable to use an alkoxide compound including silicon.

As the alkoxide compound including silicon, a compound represented by the following general formula 3 is preferable.

$$Si(OR)_4 \qquad \text{formula 3}$$

In formula 3, each R independently represents an alkyl group. The alkyl group is preferably an alkyl group having 1 to 4 carbon atoms, and is more preferably an ethyl group.

Specific examples of the alkoxide compound including silicon include tetramethoxysilane, tetraethoxysilane, tetrapropoxisilane, and the like. Among these, it is preferable to use tetraethoxysilane.

One type of the above-described compound including the element Z may be used alone, or two or more types may be used in combination.

The amount of the compound including the element Z that is used is, with respect to the total amount (moles) of the compound including the element X and the compound including the element Z, preferably 80 to 99.9 mol %, more preferably 85 to 99.5 mol %, and further preferably 94 to 99.5 mol %. In addition, when two or more of the compound including the element Z are included in combination, it is preferable that the sum thereof is included in the above range.

Compound Including Zinc

Examples of the compound including zinc include, but are not particularly limited to: inorganic salts, such as a chloride, a sulfide, a nitrate, or a carbonate of zinc; organic salts, such as an oxate, an acetylacetonato salt, a dimethyl glyoxime salt, or an ethylenediamine acetate of zinc; chelate compounds of zinc; carbonyl compounds of zinc; cyclopentadienyl compounds of zinc; ammine complexes of zinc; alkoxide compounds of zinc; alkyl compounds of zinc, and the like.

Specifically, examples include zinc chloride ($ZnCl_2$), zinc sulfide (ZnS), zinc nitrate ($Zn(NO_3)_3$), and the like.

One type of the above-described compound including zinc may be used alone, or two or more types may be used in combination.

The amount of the compound including zinc that is used is, with respect to the total amount (moles) of the compound including the element X, the compound including the element Z, and the compound including zinc, preferably 0.1 to 20 mol %, more preferably 0.5 to 15 mol %, and further preferably 0.5 to 6 mol %.

Surfactant

By using a surfactant in the production of the catalyst, a catalyst having mesopores can be obtained. More specifically, micelles are formed through the addition of the surfactant, and the obtained micelles serve as a mold with a precursor of a complex oxide formed on the surface thereof. By performing the firing described later on such a precursor, the surfactant can be removed to produce a catalyst having mesopores. Depending on the density, the shape of the micelles is spherical, cylindrical, lamellar, gyroidal, or vesicle-shaped.

Examples of the surfactant include, but are not particularly limited to, cationic surfactants, non-ionic surfactants, and the like.

Examples of the cationic surfactant include cationic surfactants conventionally used for the synthesis of mesoporous silica, such as MCM-41, SBA-15, FMS-16, and the like.

Examples of the non-ionic surfactant include, but are not particularly limited to, a polyalkylene oxide block copolymer having an alkylene oxide chain as a constituent part, a compound formed into an ether with an alcohol, a phenol, or the like on the end of the block copolymer, and the like.

In addition, one type of the alkylene oxide chain included as a constituent unit may be used alone, or two or more types may be used in combination.

Among these, from the viewpoint of the stability of the crystal structure of the pore wall forming the mesopores of the obtained complex oxide, it is preferable to use a non-ionic surfactant, and it is more preferable to use a polyalkylene oxide block copolymer. From the viewpoint of the stability of the crystal structure of the pore wall forming the mesopores of the obtained complex oxide, it is more preferable to use a polyalkylene oxide block copolymer having a polyethylene oxide chain $(CH_2CH_2O)_m$ and a polypropylene oxide chain $(CH_2CH(CH_3)O)_n$ as constituent units. Here, m and n are 1 to 1000, preferably m is 1 to 200, and n is 1 to 100. More preferably, m is 1 to 200, n is 1 to 100, and m+n is 2 to 300. An end of the polymer is formed as an ether with a hydrogen atom, a hydroxyl group, or an alcohol or phenol.

Among the above-described polyalkylene oxide block copolymers, from the viewpoint of the stability of the crystal structure of the pore wall forming the mesopores of the obtained complex oxide, a polyalkylene oxide block copolymer represented by the following general formula 4 is preferable.

$$HO(CH_2CH_2O)_r(CH_2CH(CH_3)O)_s(CH_2CH_2O)_tH \qquad \text{formula 4}$$

From the viewpoint of forming the above-described preferable average pore size of the synthesis catalyst of the present invention, r is preferably 1 to 100, s is preferably 1 to 100, and t is preferably 1 to 100. Further, r+s+t is preferably 3 to 300.

The method for obtaining the polyalkylene oxide block copolymer is not particularly limited, and a polyalkylene oxide block copolymer produced using a conventionally known production method may be used, or a commercially available product may be used.

Examples of commercially available polyalkylene oxide block copolymers include the product P123 [(HO$(CH_2CH_2O)_{20}(CH_2CH(CH_3)O)_{70}(CH_2CH_2O)_{20})H$], the product P85 [(HO$(CH_2CH_2O)_{26}(CH_2CH(CH_3)O)_{39}$ $(CH_2CH_2O)_{26})H$], and the product P103 [(HO($CH_2$ $CH_2O)_{56}(CH_2CH(CH_2)O)_{17}(CH_2CH_2O)_{56}H$)], which are manufactured by BASF.

One type of the above-described surfactant may be used alone, or two or more types may be used in combination.

The shape and pore diameter of the mesopores can be controlled by appropriately changing the type of above-described surfactant and the like.

The amount of the surfactant that is used is, based on the assumption of attaining the above-described mass ratio between the compound including the element Z and the surfactant (compound including the element Z/surfactant), with respect to 100 parts by mass of solvent, preferably 3 to 20 parts by mass, more preferably 5 to 18 parts by mass, and further preferably 7 to 15 parts by mass. It is preferable that the amount of the surfactant that is used is 3 parts by mass or more because the mesopores can be uniformly formed. On the other hand, it is preferable that the amount of the surfactant that is used is 20 parts by mass or less because the surfactant can be dissolved.

Solvent

The solvent includes water. The solvent may further include an organic solvent.

The water is not particularly limited, but ion-exchanged water from which metal ions and the like have been removed, or distilled water, is preferable.

Examples of the organic solvent include, but are not particularly limited to, aliphatic linear alcohols such as methanol, ethanol, n-propanol, and n-hexanol.

Among these, from the viewpoint of handleability, the organic solvent is preferably methanol or ethanol.

One type of the organic solvent may be used alone, or two or more types may be used in combination.

The amount of water that is used is, with respect to 1 part by mass of the surfactant, preferably 5 to 35 parts by mass, and more preferably 5 to 20 parts by mass. It is preferable that the amount of water that is used is 5 parts by mass or more because the surfactant can be dissolved. On the other hand, it is preferable that the amount of water that is used is 35 parts by mass or less because the mesopores can be uniformly formed.

The amount of water that is used is, with respect to the total amount (moles) of the compound including the element X and the compound including the element Z, preferably 100 mol % to 10000 mol %, and more preferably 1000 to 8000 mol %. It is preferable that the amount of water that is used is 100 mol % or more because hydrolysis can be performed. On the other hand, it is preferable that the amount of water that is used is 10000 mol % or less because the solids do not dissolve.

Further, when an organic solvent that is used is included as the solvent, the amount of the organic solvent is, with respect to the water, preferably 10 to 50% by volume, and more preferably 10 to 25% by volume. It is preferable that the amount of organic solvent that is used is 10% or more by volume because the element X and element Z can be dissolved. On the other hand, it is preferable that the amount of organic solvent that is used is 50% by volume or less because hydrolysis can be performed.

Acidic Solution

The acidic solution has the function of promoting the production of solids by hydrolysis, which is described later.

Examples of the acidic solution include, but are not particularly limited to, an aqueous solution in which an inorganic acid such as hydrogen chloride, sulfuric acid, nitric acid, or phosphoric acid is dissolved.

The amount of the acidic solution that is used is an amount by which the number of moles of acid included in the acidic solution becomes, with respect to the total amount (moles) of the compound including the element X and the compound including the element Z, preferably 0.01 to 10.0 mol %, and more preferably 0.1 to 8.0 mol %.

Basic Solution

The basic solution has the function of promoting the production of solids by hydrolysis, which is described later. Generally, any one of the above-described acidic solution and a basic solution is used.

Examples of the basic solution include, but are not particularly limited to, an aqueous solution in which an inorganic base such as sodium hydroxide, calcium hydroxide, or ammonia is dissolved.

The amount of the basic solution that is used is an amount that becomes, with respect to the total amount (moles) of the compound including the element X and the compound including the element Z, preferably 0.01 to 10.0 mol %, and more preferably 0.1 to 8.0 mol %.

(Preparation of Solid Colloid)

The solid colloid can be obtained by filtering, appropriately washing, and drying the above-described suspension.

By performing a step of preparing a solid colloid in this way, the catalyst can have better uniformity compared with when the suspension is directly fired. As used herein, "solid colloid" means that the amount of solvent contained in the solid colloid is 5% or less of the total volume of the solid colloid.

The drying temperature for obtaining the solid colloid is preferably 20 to 200° C., and more preferably 50 to 150° C.

The drying time is preferably 1 hour to 10 days, and more preferably 2 hours to 5 days. By setting to be in the above ranges, the solvent is removed, a sufficient mesopore diameter can be obtained in the subsequent firing step, and the specific surface area can be increased.

[Firing Step]

The firing step is a step of firing the solid colloid. By firing the solid colloid, the surfactant used as the mold is removed, and the catalyst according to the present embodiment can be produced.

The firing temperature is preferably 200 to 800° C., and more preferably 400 to 600° C. It is preferable that the firing temperature is not less than 200° C. because impurities derived from the surfactant do not remain, or hardly remain, in the catalyst. On the other hand, it is preferable that the firing temperature is not more than 800° C. because the stability of the crystal structure of the pore wall forming the mesopores of the catalyst can be improved.

Here, the rate of temperature increases up to the firing temperature is preferably 0.1 to 100° C./min, more preferably 0.5 to 50° C./min, and further preferably 1 to 20° C./min. By setting to be in the above range, there is no temperature difference between the surface and the inside of the formed article, and a sufficient mesoporous diameter can be obtained. As a result, the specific surface area of the catalyst can also be increased.

The firing time is preferably 10 minutes to 2 days, and more preferably 1 to 10 hours. It is preferable that the firing time is not less than 10 minutes because impurities derived from the surfactant do not remain, or hardly remain, in the catalyst. On the other hand, it is preferable that the firing time is not more than 2 days because the stability of the crystal structure of the pore wall forming the mesopores of the catalyst can be improved.

(Diene Compound Production Apparatus)

The diene compound production apparatus includes a reaction tube filled with the above-described catalyst. By such a production apparatus, a diene compound is produced from the raw material.

Hereinafter, a butadiene production apparatus, which is an example of the diene compound production apparatus, will be described with reference to FIG. 1.

A butadiene production apparatus 10 (hereinafter, simply referred to as the "production apparatus 10") of the present embodiment includes a reaction tube 1, a feed tube 3, a discharge tube 4, a temperature control unit 5, and a pressure control unit 6.

A reaction bed 2 is included inside the reaction tube 1. The reaction bed 2 is filled with the synthesis catalyst of the present invention. The feed tube 3 is connected to the reaction tube 1. The discharge tube 4 is connected to the reaction tube 1. The temperature control unit 5 is connected to the reaction tube 1. The discharge tube 4 includes the pressure control unit 6.

The reaction bed 2 may have only the catalyst according to the present embodiment, or may have a catalyst other than the catalyst according to the present embodiment together with the catalyst according to the present embodiment. Further, the reaction bed 2 may further have a dilution material. The dilution material prevents the catalyst from excessively generating heat.

The dilution material is, for example, quartz sand, alumina balls, aluminum balls, aluminum shots, and the like.

When the dilution material is filled into the reaction bed 2, the mass ratio represented by the dilution material/ synthesis catalyst is determined taking into consideration the type and specific gravity of each of those, and for example, 0.5 to 5 is preferable.

The reaction bed may be a fixed bed, a moving bed, a fluidized bed, or the like.

The reaction tube 1 is preferably composed of a material inert to the raw material and the synthesized product. The reaction tube 1 preferably has a shape that is capable of withstanding heating at about 100 to 600° C. and pressurization of about 10 MPa. The reaction tube 1 is, for example, a substantially cylindrical member made of stainless steel.

The feed tube 3 is feed means for feeding the raw material into the reaction tube 1. The feed tube 3 is, for example, a tube made of stainless steel.

The discharge tube 4 is discharge means for discharging a gas including the product synthesized at the reaction bed 2. The discharge tube 4 is, for example, a tube made of stainless steel or the like.

The temperature control unit 5 may be capable of setting the reaction bed 2 in the reaction tube 1 to any temperature. For example, the temperature control unit 5 controls the temperature of an electric furnace or the like (not shown) provided around the reaction tube 1, and adjusts the reaction bed 2 in the reaction tube 1 to any temperature.

The pressure control unit 6 may be capable of making the pressure in the reaction tube 1 any pressure. The pressure control unit 6 is, for example, a known pressure valve or the like.

The production apparatus 10 may include a known device such as a gas flow control unit that adjusts the flow rate of a gas, such as mass flow.

<Method for Producing Diene Compound>

According to one mode of the present invention, there is provided a method for producing a diene compound. The method for producing the diene compound includes contacting the catalyst according to the present invention with a raw material including an alcohol to produce a diene compound.

[Catalyst]

As the catalyst, the above-described catalyst is used, and therefore a description thereof is omitted here.

The amount of catalyst that is used is, with respect to the raw material, preferably 0.1 to 10 g/g·h, and more preferably 1 to 5 g/g·h. It is preferable that the amount of catalyst used is 0.1 g/g·h or more because the reaction conversion rate can be improved. On the other hand, it is preferable that the amount of catalyst used is 10 g/g·h or less because the generation of by-products can be suppressed.

[Raw Material]

The raw material includes an alcohol. In addition, the raw material may further include an aldehyde, an inert gas, and the like. It is preferable that the raw material is in a gas state (also referred to as "raw material gas") at least at the time of reaction.

(Alcohol)

Examples of the alcohol include, but are not particularly limited to, alcohols having 1 to 6 carbon atoms. Specific examples of the alcohol include methanol, ethanol, propanol, butanol, pentanol, hexanol, and the like.

In principle, the diene compound that is obtained differs depending on the alcohol that is used. For example, when ethanol is used, butadiene is obtained. In addition, when propanol is used, hexadiene is obtained. Furthermore, when butanol is used, octadiene is obtained.

One type of alcohol may be used alone, or two or more types may be used in combination. However, from the viewpoint of suppressing side reactions, it is preferable to use one type of alcohol alone.

The concentration of the alcohol in the raw material is, with respect to 100% by volume of the raw material, preferably 10% by volume or more, more preferably 15% by volume or more, further preferably 20% by volume or more, and most preferably 30% by volume or more. When two or more types of the alcohol are used in combination, it is preferable that the sum thereof is included in the above range. By using the catalyst according to the present invention, the reaction can be efficiently progressed even when the alcohol concentration in the raw material is high.

(Aldehyde)

Aldehydes are usually an oxidation product of an alcohol. Specific examples include formaldehyde, acetaldehyde, propionaldehyde, butyraldehyde, valeraldehyde, and the like.

When the raw material includes an aldehyde, generally, the aldehyde corresponding to the alcohol is included. Specifically, when methanol is used as the alcohol, formaldehyde is the aldehyde, in the case of ethanol, acetaldehyde is the aldehyde, in the case of propanol, propionaldehyde is the aldehyde, in the case of butanol, butyraldehyde is the aldehyde, and in the case of pentanol, valeraldehyde is the aldehyde. However, the aldehyde may include an aldehyde other than the aldehyde corresponding to the alcohol.

The aldehyde concentration in the raw material is, with respect to 100% by volume of the raw material, preferably 1% by volume or more, preferably 5% by volume or more, more preferably 10% by volume or more, and most preferably 30% by volume or more. When two or more types of alcohol are used in combination, it is preferable that the sum of those alcohols is included in the above range.

The total concentration of the alcohol and the aldehyde in the raw material is, with respect to 100% by volume of the raw material, preferably 15% by volume or more, and more preferably 20% by volume or more, and further preferably 20 to 40% by volume.

(Inert Gas)

Examples of the inert gas include, but are not particularly limited to, nitrogen gas, argon gas, and the like. One type of these inert gases may be used alone, or two or more types may be used in combination.

The concentration of the inert gas is, with respect to 100% by volume of the raw material, preferably 90% by volume or less, more preferably 30 to 90% by volume, further preferably 50 to 90% by volume, and particularly preferably 60 to 80% by volume.

[Contact]

The mode of contacting the catalyst with the raw material is not particularly limited, but for example, it is preferable to flow the raw material over a reaction bed in a reaction tube to contact the raw material with the synthesis catalyst in the reaction bed.

The temperature (reaction temperature) when the raw material is contacted with the catalyst is preferably 100 to 600° C., more preferably 200 to 500° C., and further preferably 250 to 450° C. It is preferable that the reaction temperature is 100° C. or more because the reaction rate is sufficiently high and the diene compound can be produced more efficiently. On the other hand, it is preferable that the reaction temperature is 600° C. or lower because deterioration of the catalyst can be prevented or suppressed.

The pressure (reaction pressure) when the raw material is contacted with the catalyst is preferably 0.1 to 10 MPa, and more preferably 0.1 to 3 MPa. It is preferable that the reaction pressure is 0.1 MPa or more because the reaction rate is high and the diene compound can be produced more efficiently. On the other hand, it is preferable that the reaction pressure is 10 MPa or less because deterioration of the catalyst can be prevented or suppressed.

The spatial velocity (SV) of the raw material in the reaction bed is generally adjusted as appropriate in consideration of the reaction pressure and reaction temperature, but in terms of standard state, is preferably set to be 0.1 to 10000 $h^{-1}$.

For example, when using production apparatus 10 to produce butadiene, the insides of the reaction tube 1 is set to any temperature and any by the temperature control unit 5 and the pressure control unit 6. A gasified raw material 20 is supplied from the feed tube 3 into the reaction tube 1. In reaction tube 1, the raw material is contacted with the synthesis catalyst and reacted to produce a diene compound such as butadiene. A production gas 22 including the diene compound such as butadiene is discharged from the discharge tube 4. The production gas 22 may also include compounds such as acetaldehyde, propylene, ethylene, and the like.

The production gas including the diene compound (production gas 22 in FIG. 1) is subjected to purification, such as gas liquid separation or distillation purification, as necessary, and unreacted raw materials and by-products are removed.

Further, the present invention can also produce a diene compound from bioethanol to reduce environmental impact.

<Method for Producing Polymer>

According to one embodiment of the present invention, a method for producing a polymer is provided. The method for producing a polymer includes producing a polymer by using at least a portion of the diene compound produced by the above-described method for producing a diene compound as a polymer raw material.

That is, the method for producing a diene compound according to the present invention is applied in the production of a diene compound by contacting a raw material including an alcohol with the catalyst according to the present invention. The diene compound obtained by the method for producing a diene compound according to the present invention is subjected as appropriate to a separation treatment from the reaction product and the like, and a polymer is produced using at least a portion thereof as a raw material.

As the method for separating from the reaction product, it is preferable to pass the product through a cooled condenser, separate the raw material such as unreacted ethanol, bubble the separated product into an organic solvent, dissolve the diene compound (monomer) in the solvent, and recover as a solution.

It is preferable that the solution containing the recovered diene compound is subjected as is, or after further adding an organic solvent or the like, to various types of polymerization to produce the polymer from the diene compound. At this time, the various types of polymerization may be performed by mixing monomers other than the diene compound with the recovered diene compound.

As the polymerization method, any method can be used, such as solution polymerization, suspension polymerization, liquid phase mass polymerization, and emulsification polymerization. Further, when a solvent is used for the polymerization reaction, a solvent inert in the polymerization reaction is used, for example, hexane, cyclohexane, toluene, mixtures thereof, and the like.

The polymerization temperature is not particularly limited, and is in the range of −100° C. to 300° C. The pressure of the polymerization reaction is not particularly limited, and in the range of 0.1 to 10.0 MPa. The reaction time of the polymerization reaction is not particularly limited, and is appropriately adjusted according to conditions such as polymerization temperature, but is usually in the range of 1 second to 10 days.

Here, examples of the monomer other than the diene compound include a monomer selected from a group consisting of aromatic vinyl compounds, olefins, and combinations thereof. Examples of the aromatic vinyl compound include styrene, α-methylstyrene, p-methyl styrene, and vinyl naphthalene. As the olefin, ethylene, propylene, 1-butene, 1-pentene, 1-hexene, 1-hepten, 1-octene, and the like can be used.

In addition to the above-described monomers, various additives may be added in accordance with the application.

The polymer obtained by the method for producing a polymer according to the present invention is not particularly limited as long as it is obtained using the above-described diene compound, but a polymer having a skeleton derived from butadiene is preferable, and polybutadiene (cis-1,4-polybutadiene), styrene-butadiene copolymer, and the like are preferable.

<Method for Producing Polymer Formed Article>

According to one embodiment of the present invention, a method for producing a polymer formed article is provided. The method for producing the polymer formed article includes forming a polymer produced by the above-described method for producing a polymer of the present invention.

That is, the method for producing a diene compound according to the present invention is applied in the production of a diene compound by contacting a raw material including an alcohol with the catalyst according to the present invention. Further, the method for producing a polymer of the present invention is applied in the production of a polymer using at least a portion of the diene compound as a polymer raw material. The polymer produced by the method for producing a polymer according to the present invention uses known forming means in accordance with the form of the desired polymer formed article.

Here, examples of the polymer formed article include a rubber member of a tire, such as a tread, a base tread, a sidewall, a side reinforcement, a bead filler, a tire, an anti-vibration rubber, seismic isolation rubber, a belt (conveyor belt), a rubber crawler, various hoses, and the like, and a rubber member of a tire or a tire is preferable.

<<Second Invention>>

<Catalyst>

The catalyst according to the present embodiment includes at least one element X selected from the group consisting of Groups 3 to 6 of the Periodic Table and at least one element Z selected from the group consisting of Group 14 elements. By containing the element X, the raw material can be converted into a diene compound. Further, by including the element Z, the contact area between the raw material and the catalyst can be increased.

The catalyst according to the present embodiment has mesopores, and in particular the average pore size of the catalyst is 2 to 20 nm, preferably 2 to 15 nm, and more preferably 8 to 13 nm. By setting the average pore size to be 2 to 20 nm, in particular, a high frequency of collisions among the raw material in the pores can be achieved while avoiding a state in which an excessive progression of reaction progresses. As a result, it is conjectured that a high catalytic activity can always be maintained because it is possible to avoid a deterioration in activity due to the polymers which are produced in an excessive progression of reaction poisoning the active metal.

Here, the "average pore size" of the catalyst is a value measured by the following method. That is, the average pore size is calculated from the total pore volume (sum of the pore volume of the catalyst) and the BET specific surface area.

Specifically, the average pore size can be calculated by assuming that the pores have a cylindrical shape (BJH method). The average pore size can then be calculated by $4V1/A1$, in which a BET specific surface area A1 is taken to be the surface area of the side of the cylinder and a total pore volume V1 is taken to be the volume of the cylinder.

The total pore volume of the catalyst is preferably 0.1 to 10.0 mL/g, more preferably 0.1 to 5.0 mL/g, and further preferably 0.1 to 2.0 mL/g. The total pore volume is preferably 0.1 mL/g or more because the diffusibility of the alcohol is improved, and the raw material conversion rate and diene compound selectivity are further increased. On the other hand, the total pore volume is preferably 10.0 mL/g or less because the contact area between the alcohol and the catalyst increases, and the raw material conversion rate and diene compound selectivity are further increased.

The BET specific surface area of the catalyst (hereinafter, sometimes simply referred to as "specific surface area") is 700 to 1200 $m^2/g$, preferably 720 to 1150 $m^2/g$, and more preferably 800 to 1100 $m^2/g$.

In particular, by setting the BET specific surface area to be 700 to 1200 $m^2/g$, there are sufficient numbers of active points on the catalyst surface, so that the raw material conversion rate and diene compound selectivity are further increased. As a result, the raw material conversion rate increases even if the content of the raw material is a high concentration with respect to 100% by volume (gas equivalent) of the raw material, and for example, a high raw material conversion rate is exhibited even at 100% by volume.

The product of the total pore volume and the specific surface area of the catalyst is preferably 10 to 100000 $mL·m^2/g^2$, more preferably 20 to 25000 $mL·m^2/g^2$, and further preferably 20 to 2000 $mL·m^2/g^2$. The product is preferably 10 $mL·m^2/g^2$ or more because there are sufficient numbers of active points on the catalyst surface and the diffusibility of the raw material including an alcohol is improved, so that the raw material conversion rate and diene compound selectivity are further increased. On the other hand, the product is preferably 100000 $mL·m^2/g^2$ or less because the contact area between the raw material and the catalyst tends to be sufficient, and the raw material conversion rate and diene compound selectivity are further increased.

The mesopore volume ratio (total mesopore volume/total pore volume×100) of the catalyst is preferably 50% or more, more preferably 50 to 100%, further preferably 80 to 100%, and particularly preferably 90 to 100%. The mesopore volume ratio is preferably 50% or more because sufficient mesopores are present in the catalyst, and the diffusibility of the raw material including an alcohol is improved, so that the raw material conversion rate and diene compound selectivity are further increased.

The mesopore pore volume ratio can be controlled based on the usage ratio of the raw material (compound including X, compound including Z, etc.) in the production method described later, firing temperature in the firing step, and the like.

The shape of the mesopores of the catalyst and whether the pore wall forming the mesopores has a crystal structure having a regular arrangement can be confirmed by observing the diffraction peaks by X-ray diffraction. Specifically, when the pore wall forming the mesopores of the synthesis catalyst has a crystal structure having a regular arrangement, it is preferable that a peak derived from the periodic structure of the mesopores is observed in a low angle range of $\theta=6°$ or less (preferably 1° to 6°, and more preferably 0.1° to 1°) by X-ray diffraction.

Specifically, it is preferable that at least one diffraction peak is observed in a low angle range of $\theta=6°$ or less in the X-ray diffraction profile observed using X-ray diffraction, and that the ratio (I/H) of the peak intensity I of the at least one diffraction peak to the half width at half maximum H of the diffraction peak is 5000 or more.

Further, the shape and regularity of the mesopores can be confirmed by observing the synthesis catalyst with a transmission electron microscope (TEM).

Further, it is preferable that at least one diffraction peak having a half width at half maximum of 1° or more is observed in a high angle range of $\theta=10°$ to 40°, and preferably in the range of $\theta=20°$ to 25°, in an X-ray diffraction profile of the catalyst observed using X-ray diffraction. This diffraction peak is due to the complex oxide including the element X and the element Y. The presence of this complex oxide suppresses an excessive progression of reaction to the polymer that tends to progress on the aggregate of the single oxide of the element X, thereby enabling the diene compound to be selectively obtained in a high yield.

It is preferable that a diffraction peak due to the single oxide of the element X is not observed in the high angle range of $\theta=10°$ to 40°. When such a diffraction peak is not observed, this means that most of the element X is a component of the complex oxide, and the conversion function of the element X into a diene compound can be sufficiently exhibited. Further, the excessive progression of reaction of the element X to a polymer that tends to progress on the aggregate of the single oxide (for example, hafnium oxide etc.) is suppressed.

Here, the fact that no diffraction peak due to the single oxide of the element X is observed means that the ratio (I/H) of the peak intensity I of the diffraction peak to the half width at half maximum H of the diffraction peak is 900 or less.

Crystallinity increases as the half width at half maximum of the diffraction peak becomes smaller, but in the present embodiment, the half width at half maximum is preferably 6° to 12°, and more preferably 7° to 11°.

Since the half width at half maximum is 6° to 12°, there is a gap between each of the elements constituting complex oxide, and hence it is conjectured that the reaction to the diene compound tends to progress selectively.

Of the diffraction peaks, the ratio (I/H) of the peak intensity I of the largest diffraction peak with the maximum diffraction intensity to the half width at half maximum H of that maximum diffraction peak is preferably 1000 to 3000, and more preferably 1500 to 2200.

Since the ratio (I/H) is 1000 to 3000, the reaction to butadiene tends to selectively progress.

Here, examples of the element X include Group 3 elements such as scandium (Sc), yttrium (Y), lanthanum (La), and cerium (Ce); Group 4 elements such as titanium (Ti), zirconium (Zr), and hafnium (Hf; Group 5 elements such as vanadium (V), niobium (Nb), and tantalum (Ta); and Group 6 elements such as chromium (Cr), molybdenum (Mo), and tungsten (W). Of these, the element X is preferably a Group 3 element, a Group 4 element, or a Group 5 element, more preferably a Group 4 element or a Group 5 element, and further preferably a Group 4 element.

Further, according to another embodiment, the element X is preferably a Period 5 element, a Period 6 element, or a Period 7 element, and more preferably a Period 5 element or a Period 6 element. Specifically, the element X is preferably yttrium (Y), lanthanum (La), cerium (Ce), titanium (Ti), zirconium (Zr), hafnium (Hf), vanadium (V), niobium (Nb), tantalum (Ta), molybdenum (Mo), or tungsten (W), more preferably yttrium (Y), lanthanum (La), cerium (Ce), titanium (Ti), zirconium (Zr), hafnium (Hf), niobium (Nb), or tantalum (Ta), further preferably zirconium (Zr), hafnium (Hf), niobium (Nb), or tantalum (Ta), particularly preferably zirconium (Zr), hafnium (Hf), or niobium (Nb), very preferably niobium (Nb) or hafnium (Hf), and most preferably hafnium (Hf).

The element X may include one type alone or may include two or more types in combination.

Examples of the element Z include carbon (C), silicon (Si), germanium (Ge), and tin (Sn).

Of these, the element Z is preferably carbon (C) or silicon (Si), and more preferably silicon (Si).

One type of the element Z may be included, or two or more types may be included in combination.

Further, a particularly preferable combination is Hf as the element X and Si as the element Z.

The molar content $(X/(X+Z)\times100)$ of the element X with respect to the total amount (moles) of the element X and the element Z in the catalyst is preferably 0.1 to 20 mol %, more preferably 0.5 to 15 mol %, further preferably 0.5 to 6 mol %, and particularly preferably 0.7 to 4 mol %.

When two or more of the element X are included in combination and two or more of the element Z are included in combination, the molar content is calculated based on the sum of those two or more of the element X and two or more of the element Z.

In one preferred embodiment, the catalyst preferably satisfies the following general formula 1.

$$X_{a1}Si_{b1}O_{\delta1} \qquad \text{formula 1}$$

In formula 1, X represents the element X.

a1 is the molar ratio of the element X, and when the sum of a1 and b1 is 100 mol %, a1 is preferably 0.1 to 20 mol %, more preferably 0.5 to 15 mol %, further preferably 0.5 to 6 mol %, and particularly preferably 0.7 to 4 mol %.

b1 is the molar ratio of Si, and when the sum of a1 and b1 is 100 mol %, b1 is preferably 80 to 99.9 mol %, more preferably 85 to 99.5 mol %, further preferably 94 to 99.5 mol %, and particularly preferably 94 to 99.3 mol %.

$\delta1$ represents the number required to satisfy the charge neutral condition. Specifically, $\delta1$ is defined by the elements X and Si constituting the catalyst, and a1 and b1. For example, $\delta1$ is preferably 100 to 2000, more preferably 100 to 1000, and further preferably 100 to 400.

The fact that the molar content of the element X and the catalyst are represented by general formula 1 can be confirmed by, for example, light emission spectroscopy or X-ray fluorescence measurement.

To the extent that the effects of the present invention are not impaired, the catalyst of the present embodiment may include elements other than the element X and the element Z, such as the element zinc (Zn), as constituent elements of the complex oxide.

In addition, when elements other than the element X and the element Z are included as the constituent elements of complex oxide (hereinafter, such elements are referred to as "other elements"), regarding the molar ratio of the element X, the element Z, and the other elements, it is preferable that the molar ratio of the element Z is reduced by the molar ratio of the other elements, as described above. In other words, the molar ratio of the element X is preferably the same molar ratio regardless of whether or not other elements are included. This is the same even when two or more other elements are included.

The above-described catalyst is preferably a catalyst for synthesizing a diene compound that synthesizes a diene compound from a raw material including an alcohol. In such a case, as described later, it is preferable to include ethanol and/or an acetaldehyde as the alcohol, and it is more preferable to include ethanol. Further, as described later, it is preferable that the diene compound is 1,3-butadiene.

<Method for Producing Catalyst>

It is preferable that the catalyst according to the present embodiment is produced by carrying out a solid colloid preparation step and a firing step. The solid colloid preparation step and the firing step are the same as in the <Method for producing catalyst> according to the first invention. In particular, in order to set the BET specific surface area to be 700 to 1200 m²/g and the average pore size to be 2 to 20 nm, it is necessary to give consideration to (A) the stirring speed of the raw material solution when adding the compound including the element Z, (B) the drying temperature and drying time for obtaining the solid colloid, and (C) the firing conditions in the firing step (in particular, the rate of temperature increase to the firing temperature) in the <Method for producing catalyst> according to the first invention.

The stirring speed of the raw material solution when adding the compound including the element Z is, as described in the <Method for producing catalyst> according to the first invention, preferably 10 to 2000 rpm, more preferably 10 to 1000 rpm, and further preferably 10 to 500 rpm. By being in the above range, the hydrolysis of the compound including the element Z is not too early, an interaction with the surfactant occurs so that mesopores having an average pore size of 2 to 20 nm are obtained, and a specific surface area of 700 to 1200 m³/g tends to be obtained.

Further, as described in the (Preparation of solid colloid) in the <Method for producing catalyst> according to the first invention, the drying temperature for obtaining the solid colloid is preferably 20 to 200° C., and more preferably 50 to 150° C.

The drying time is preferably 1 hour to 10 days, and more preferably 2 hours to 5 days.

In the above ranges, the solvent is removed, mesopores having an average pore size of 2 to 20 nm are obtained in the subsequent firing process, and a specific surface area of 700 to 1200 m²/g tends to be obtained.

In addition, as described in the (Firing step) in the <Method for producing catalyst> according to the first invention, the firing temperature is preferably 200 to 800° C., and more preferably 400 to 600° C. It is preferable that the firing temperature is not less than 200° C. because impurities derived from the surfactant do not remain, or hardly remain, in the catalyst. On the other hand, it is preferable that the firing temperature is not more than 800° C. because the stability of the crystal structure of the pore wall forming the mesopores of the catalyst can be improved.

By setting to be in the above range, mesopores having an average pore size of 2 to 20 nm are obtained, and a specific surface area of 700 to 1200 m/g tends to be obtained.

(Diene Compound Production Apparatus)

The diene compound production apparatus includes a reaction tube filled with the above-described catalyst. By such a production apparatus, a diene compound is produced from the raw material. The production apparatus of the diene compound is the same as that of the (Diene compound production apparatus) according to the first invention.

<Method for Producing Diene Compound>

According to one mode of the present invention, a method for producing a diene compound is provided. The method for producing the diene compound is the same as that of the <Method for producing diene compound> according to the first invention.

<Method for Producing Polymer>

According to one embodiment of the present invention, a method for producing a polymer is provided. The method for producing the polymer is the same as that of the <Method for producing polymer> according to the first invention.

<Method for Producing Polymer Formed Article>

According to one embodiment of the present invention, a method for producing a polymer formed article is provided. The method for producing the polymer formed article is the same as that of the <Method for producing polymer formed article> according to the first invention.

<<Third Invention>>

<Catalyst>

The catalyst according to the present embodiment includes at least one element X selected from the group consisting of Groups 3 to 6 of the Periodic Table and at least one element Z selected from the group consisting of Group 14 elements. By containing the element X, the raw material can be converted into a diene compound. Further, by including the element Z, the contact area between the raw material and the catalyst can be increased.

Further, at least one diffraction peak having a half width at half maximum of 1 or more is observed in a high angle range of $\theta=10°$ to 40°, and preferably in the range of $\theta=20°$ to 25°, in an X-ray diffraction profile of the catalyst observed using X-ray diffraction. This diffraction peak is due to the complex oxide including the element X and the element Y. The presence of this complex oxide suppresses an excessive progression of reaction to the polymer that tends to progress on the aggregate of the single oxide of the element X, thereby enabling the diene compound to be selectively obtained in a high yield. The conditions of the X-ray diffraction are as described in the examples.

It is preferable that a diffraction peak due to the single oxide of the element X is not observed in the high angle range of $\theta=10°$ to 40°. When such a diffraction peak is not observed, this means that most of the element X is a component of the complex oxide, and the conversion function of the element X into a diene compound can be sufficiently exhibited. Further, the excessive progression of reaction of the element X to a polymer that tends to progress on the aggregate of the single oxide (for example, hafnium oxide etc.) is suppressed.

Here, the fact that no diffraction peak due to the single oxide of the element X is observed means that the ratio (I/H) of the peak intensity I of the diffraction peak to the half width at half maximum H of the diffraction peak is 900 or less. In addition, the half width at half maximum when a diffraction peak due to the single oxide of the element X is observed is, for example, about 0.01 to 1.0.

Crystallinity increases as the half width at half maximum of the diffraction peak becomes smaller, but in the present embodiment, the half width at half maximum is preferably 6° to 12°, and more preferably 7° to 11°.

Since the half width at half maximum is 6° to 12°, there is a gap between each of the elements constituting complex oxide, and hence it is conjectured that the reaction to the diene compound tends to progress selectively.

Of the diffraction peaks, the ratio (I/H) of the peak intensity I of the largest diffraction peak with the maximum diffraction intensity to the half width at half maximum H of that maximum diffraction peak is preferably 1000 to 3000, and more preferably 1500 to 2200.

Since the ratio (I/H) is 1000 to 3000, the reaction to butadiene tends to selectively progress.

Here, examples of the element X include Group 3 elements such as scandium (Sc), yttrium (Y), lanthanum (La), and cerium (Ce); Group 4 elements such as titanium (Ti), zirconium (Zr), and hafnium (Hf); Group 5 elements such as vanadium (V), niobium (Nb), and tantalum (Ta); and Group 6 elements such as chromium (Cr), molybdenum (Mo), and tungsten (W). Of these, the element X is preferably a Group 3 element, a Group 4 element, or a Group 5 element, more preferably a Group 4 element or a Group 5 element, and further preferably a Group 4 element.

Further, according to another embodiment, the element X is preferably a Period 5 element, a Period 6 element, or a Period 7 element, and more preferably a Period 5 element or a Period 6 element. Specifically, the element X is preferably yttrium (Y), lanthanum (La), cerium (Ce), titanium (Ti), zirconium (Zr), hafnium (Hf), vanadium (V), niobium (Nb), tantalum (Ta), molybdenum (Mo), or tungsten (W), more preferably yttrium (Y), lanthanum (La), cerium (Ce), titanium (Ti), zirconium (Zr), hafnium (Hf), niobium (Nb), or tantalum (Ta), further preferably zirconium (Zr), hafnium (Hf), niobium (Nb), or tantalum (Ta), particularly preferably zirconium (Zr), hafnium (Hf), or niobium (Nb), very preferably niobium (Nb) or hafnium (Hf), and most preferably hafnium (Hf).

The element X may include one type alone or may include two or more types in combination.

Examples of the element Z include carbon (C), silicon (Si), germanium (Ge), and tin (Sn).

Of these, the element Z is preferably carbon (C) or silicon (Si), and more preferably silicon (Si).

One type of the element Z may be included, or two or more types may be included in combination.

Further, a particularly preferable combination is Hf as the element X and Si as the element Z.

The molar content $(X/(X+Z)\times 100)$ of the element X with respect to the total amount (moles) of the element X and the element Z in the catalyst is preferably 0.1 to 20 mol %, more preferably 0.5 to 15 mol %, further preferably 0.5 to 6 mol %, and particularly preferably 0.7 to 4 mol %.

When two or more of the element X are included in combination and two or more of the element Z are included in combination, the molar content is calculated based on the sum of those two or more of the element X and two or more of the element Z.

In one preferred embodiment, the catalyst preferably satisfies the following general formula 1.

$$X_{a1}Si_{b1}O_{\delta 1} \qquad \text{formula 1}$$

In formula 1, X represents the element X.

a1 is the molar ratio of the element X, and when the sum of a1 and b1 is 100 mol %, a1 is preferably 0.1 to 20 mol %, more preferably 0.5 to 15 mol %, further preferably 0.5 to 6 mol %, and particularly preferably 0.7 to 4 mol %.

b1 is the molar ratio of Si, and when the sum of a1 and b1 is 100 mol %, b1 is preferably 80 to 99.9 mol %, more preferably 85 to 99.5 mol %, further preferably 94 to 99.5 mol %, and particularly preferably 94 to 99.3 mol %.

δ1 represents the number required to satisfy the charge neutral condition. Specifically, δ1 is defined by the elements X and Si constituting the catalyst, and a1 and b1. For example, δ1 is preferably 100 to 2000, more preferably 100 to 1000, and further preferably 100 to 400.

The fact that the molar content of the element X and the catalyst are represented by general formula 1 can be confirmed by, for example, light emission spectroscopy or X-ray fluorescence measurement.

To the extent that the effects of the present invention are not impaired, the catalyst of the present embodiment may include elements other than the element X and the element Z, such as the element zinc (Zn), as constituent elements of the complex oxide.

In addition, when elements other than the element X and the element Z are included as the constituent elements of complex oxide (hereinafter, such elements are referred to as "other elements"), regarding the molar ratio of the element X, the element Z, and the other elements, it is preferable that the molar ratio of the element Z is reduced by the molar ratio of the other elements, as described above. In other words, the molar ratio of the element X is preferably the same molar ratio regardless of whether or not other elements are included. This is the same even when two or more other elements are included.

The catalyst according to the present embodiment preferably has mesopores. By having mesopores, the diffusibility of the raw material (alcohol, etc.) into the catalyst is improved, and the contact area between the raw material and the catalyst increases. As a result, even when the alcohol concentration is high, the raw material conversion rate and diene compound selectivity are improved. The catalyst has an average pore size of 2 to 50 nm, preferably 2 to 30 nm, more preferably 2 to 20 nm, and further preferably 2 to 15 nm. Here, the "average pore size" of the catalyst is a value measured by the following method. That is, the average pore size is calculated from the total pore volume (sum of the pore volume of the catalyst) and the BET specific surface area.

Specifically, the average pore size can be calculated by assuming that the pores have a cylindrical shape (BJH method). The average pore size can then be calculated by 4V1/A1, in which a BET specific surface area A1 is taken to be the surface area of the side of the cylinder and a total pore volume V1 is taken to be the volume of the cylinder.

The total pore volume of the catalyst is preferably 0.1 to 10.0 mL/g, more preferably 0.1 to 5.0 mL/g, and further preferably 0.1 to 2.0 mL/g. The total pore volume is preferably 0.1 mL/g or more because the diffusibility of the alcohol is improved, and the raw material conversion rate and diene compound selectivity are further increased. On the other hand, the total pore volume is preferably 10.0 mL/g or less because the contact area between the alcohol and the catalyst increases, and the raw material conversion rate and diene compound selectivity are further increased.

The specific surface area of the catalyst is preferably 100 to 10000 m²/g, more preferably 200 to 5000 m²/g, further preferably 200 to 1500 m²/g, and particularly preferably 700 to 1200 m²/g.

The specific surface area is preferably 100 m/g or more because there are sufficient numbers of active points on the catalyst surface, so that the raw material conversion rate and diene compound selectivity are further increased. As a result, the raw material conversion rate increases even if the content of the raw material is a high concentration with respect to 100% by volume (gas equivalent) of the raw material, and for example, a high raw material conversion rate is exhibited even at 100% by volume. On the other hand, the specific surface area is preferably 10000 $m^2$/g or less because the contact area between the raw material and the catalyst increases, and the raw material conversion rate and diene compound selectivity are further increased.

The product of the total pore volume and the specific surface area of the catalyst is preferably 10 to 100000 mL·$m^2$/$g^2$, more preferably 20 to 25000 mL·$m^2$/$g^2$, and further preferably 20 to 2000 mL·$m^2$/$g^2$. The product is preferably 10 mL·$m^2$/$g^2$ or more because there are sufficient numbers of active points on the catalyst surface and the diffusibility of the raw material including an alcohol is improved, so that the raw material conversion rate and diene compound selectivity are further increased. On the other hand, the product is preferably 100000 mL·$m^2$/$g^2$ or less because the contact area between the raw material and the catalyst tends to be sufficient, and the raw material conversion rate and diene compound selectivity are further increased.

The mesopore volume ratio (total mesopore volume/total pore volume×100) of the catalyst is preferably 50% or more, more preferably 50 to 100%, further preferably 80 to 100%, and particularly preferably 90 to 100%. The mesopore volume ratio is preferably 50% or more because sufficient mesopores are present in the catalyst, and the diffusibility of the raw material including an alcohol is improved, so that the raw material conversion rate and diene compound selectivity are further increased.

The mesopore volume ratio can be controlled based on the usage ratio of the raw material (compound including X, compound including Z, etc.) in the production method described later, firing temperature in the firing step, and the like.

The shape of the mesopores of the catalyst and whether the pore wall forming the mesopores has a crystal structure having a regular arrangement can be confirmed by observing the diffraction peaks by X-ray diffraction. Specifically, when the pore wall forming the mesopores of the synthesis catalyst has a crystal structure, it is preferable that a peak derived from the periodic structure of the mesopores is observed in a low angle range of θ=6° or less (preferably 0.1° to 6°, and more preferably 0.1° to 1°) by X-ray diffraction.

Specifically, it is preferable that at least one diffraction peak is observed in a low angle range of θ=6° or less in the X-ray diffraction profile observed using X-ray diffraction, and that the ratio (I/H) of the peak intensity I of the at least one diffraction peak to the half width at half maximum H of the diffraction peak is 5000 or more.

Further, the shape and regularity of the mesopores can be confirmed by observing the synthesis catalyst with a transmission electron microscope (TEM).

The above-described catalyst is preferably a catalyst for synthesizing a diene compound that synthesizes a diene compound from a raw material including an alcohol. In such a case, as described later, it is preferable to include ethanol and/or an acetaldehyde as the alcohol, and it is more preferable to include ethanol. Further, as described later, it is preferable that the diene compound is 1,3-butadiene.

<Method for Producing Catalyst>

The catalyst according to the present embodiment is produced by carrying out a solid colloid preparation step and a firing step. In the solid colloid preparation step, in order to obtain at least one of the X-ray diffraction profiles of the below (A) to (D), it is particularly preferable to prepare the raw material solution as follows. The other parts of the solid colloid preparation step and the firing step are the same as in the <Method for producing catalyst> according to the first invention.

(A) In the X-ray diffraction of the catalyst, at least one diffraction peak having a half width at half maximum of 1° or more is observed in the high angle range of θ=10° to 40°.

(B) In (A), the ratio (I/H) of the peak intensity I of the largest diffraction peak with the maximum diffraction intensity to the half width at half maximum H of that maximum diffraction peak is 1000 to 3000.

(C) In the X-ray diffraction of the catalyst, a diffraction peak due to the single oxide of the element X is not observed in the high angle range of θ=10° to 40°.

(D) In (A) or (B), the half width at half maximum is 6° to 12°.

(1) First, water and an acidic solution or a basic solution are added to a predetermined amount of surfactant, and the surfactant is dissolved by stirring at a predetermined speed (e.g., about 50 to 200 rpm) under ordinary temperature and pressure conditions.

It is preferable to add the acidic solution or basic solution so that the raw material solution to be prepared has an acidity or basicity of 0.001 mol/L to 10 mol/L (preferably 0.01 to 5 mol/L). The acidic solution or basic solution promotes the hydrolysis of precursors such as the compound including the element X and the compound including the element Z. By being in the above range, the hydrolysis rate of the metal precursors is not too high, and as a result, aggregation between single metal oxides is prevented, and the complex oxide can be efficiently obtained.

(2) The compound including the element X is added at a predetermined rate while stirring the aqueous solution in which the surfactant is dissolved at a predetermined speed under ordinary temperature and pressure conditions.

The stirring speed when stirring at the predetermined speed is preferably 10 to 2000 rpm, more preferably 10 to 1000 rpm, and further preferably 10 to 500 rpm. By setting the stirring speed to be within the above range, aggregation is prevented between single metal oxides, and the complex oxide can be efficiently obtained.

Further, the addition rate when adding the compound including the element X at a predetermined rate is preferably 0.1 to 100 mg/min, more preferably 0.1 to 50 mg/min, and further preferably 0.1 to 20 mg/min. In the above range, while being a practical addition rate, aggregation between single metal oxides is prevented, and a complex oxide can be efficiently obtained.

In addition, the concentration of the compound including the element X in the raw material solution to be prepared is preferably in the range of 0.001 to 1000 g/L, and more preferably in the range of 0.01 to 100 g/L. In the above range, while having good handling in the subsequent steps, aggregation between single metal oxides is prevented, and a complex oxide can be efficiently obtained.

(3) After confirming that all of the compound including the element X has been dissolved, the compound including the element Z is added at a predetermined rate while stirring at a predetermined rate under ordinary temperature and pressure conditions to prepare a raw material solution.

The predetermined rate when adding the compound including the element Z is preferably 0.01 to 10 g/min, more preferably 0.01 to 5 g/min, and further preferably 0.01 to 1 g/min. By setting the predetermined rate to be no more than the upper limit value of the above range, the hydrolysis reaction rate of the compound including the element Z is prevented from becoming too fast, the reaction progresses more easily around the surfactant, and it is easier to produce mesopores. By setting the predetermined rate to be no less than the lower limit value of the above range, it is possible to prevent hydrolysis with moisture in the air during the addition of the compound including the element Z.

The concentration of the compound including the element Z in the raw material solution to be prepared is preferably in the range of 0.001 to 1000 g/L, and more preferably in the range of 0.01 to 100 g/L. By setting the concentration to be no more than the upper limit value of the above range, the hydrolysis reaction rate of the compound including the element Z is prevented from becoming too fast, the reaction tends to progress around the surfactant, and it is easier to produce mesopores. By setting the concentration to be no less than the lower limit value of the above range, it is possible to prevent hydrolysis with moisture in the air during the addition of the compound including the element Z.

In addition, the compound including the element Z is added such that a mass ratio to the surfactant (compound including the element Z/surfactant) is preferably 0.01 to 100, and more preferably 0.05 to 50, further preferably 0.1 to 10. By adding such that the mass ratio is not more than the upper limit value of the above range, the compound including the element Z tends to react around the surfactant and is formed more easily. By adding such that the mass ratio is not less than the lower limit value of the above range, it is possible to prevent the formation of oxides (silica etc.) partially including the element Z due to there being too much surfactant, which results in a divided structure, and mesopores are formed more easily in the catalyst.

The stirring speed of the raw material solution when adding the compound including the element Z is preferably 10 to 2000 rpm, more preferably 10 to 1000 rpm, and further preferably 10 to 500 rpm. By being in the above range, the hydrolysis of the compound including the element Z is not too early, an interaction with the surfactant occurs so that sufficient mesopores are obtained, and the specific surface area can also be increased.

(4) Then, a suspension is obtained by aging the raw material solution. The method for obtaining the suspension is the same as the method according to the first invention.

<Method for Producing Diene Compound>

According to one mode of the present invention, a method for producing a diene compound is provided. The method for producing the diene compound is the same as that of the <Method for producing diene compound> according to the first invention.

(Diene Compound Production Apparatus)

The diene compound production apparatus includes a reaction tube filled with the above-described catalyst. By such a production apparatus, a diene compound is produced from the raw material. The production apparatus of the diene compound is the same as that of the (Diene compound production apparatus) according to the first invention.

<Method for Producing Polymer>

According to one embodiment of the present invention, a method for producing a polymer is provided. The method for producing the polymer is the same as that of the <Method for producing polymer> according to the first invention.

<Method for Producing Polymer Formed Article>

According to one embodiment of the present invention, a method for producing a polymer formed article is provided. The method for producing the polymer formed article is the same as that of the <Method for producing polymer formed article> according to the first invention.

EXAMPLES

Hereinafter, the present invention will be specifically described by using examples, but the present invention is not limited to the following description.

Examples Corresponding to First Invention (X-Ray Diffraction Line Measurement Method)

Before performing X-ray diffraction line measurement, a sample of the catalyst was prepared. First, about 100 mg of the catalyst was weighed into a mortar, and ground using a pestle to adjust the particle size to 44 µm or less. The particle size-adjusted catalyst was uniformly filled into holes in a sample filling portion of a sample plate, and adjusted so that the surface of the sample plate and the catalyst surface were in the same plane.

For the X-ray diffraction line measurement, a sample horizontal-type multipurpose X-ray diffraction device Ultima III manufactured by Rigaku Corporation was used. A copper pipe made of pure copper was used for the anticathode, and a characteristic X-ray of CuKα (wavelength $(\lambda)$=1.5418 Å (0.15418 nm)) was used for diffraction. The diffraction meter had a divergence slit of $\frac{1}{2}°$, a divergence longitudinal restriction slit of 10 mm, a scattering slit of 2°, and a light receiving slit of 0.15 mm. Then, X-rays were irradiated on the prepared catalyst sample under conditions of a tube voltage of 40 kV and a tube current of 20 mA. The scanning angle of the goniometer was set in the range of 3 to 60°, and the measurement was carried out at a scanning speed of 2°/min.

After the measurement was finished, the obtained data was analyzed. The data was displayed on a graph in Excel or the like with angle on the horizontal axis and cps on the vertical axis, and the presence or absence of a peak was confirmed. When a peak was present, the data was displayed as a graph with the cps value (intensity) on the vertical axis, and baseline correction was performed by setting the point with the lowest cps value to 0 cps. The highest value of cps was taken as the apex of the peak, and the angle and cps value of that point were confirmed. In addition, the difference between the angle of the apex of the highest peak and the angle of the location indicating the cps value of half of that cps value was calculated and taken as the half width at half maximum. When the half width at half maximum is different on the left and right of the peak, the larger value was taken as the half width at half maximum. When there was a plurality of peaks, the half width at half maximum was calculated for each of those peaks. Further, when the peaks overlapped and the half width at half maximum could not be calculated, peak fitting using a least squares method or the like was performed to separate the peaks, and then the half width at half maximum was calculated.

(Catalyst Evaluation: Diene Compound Synthesis)

Using the catalysts prepared in Examples 1-1 to 1-10 and Comparative Examples 1-1 to 1-3, 1,3-butadiene (BD) selectivity, polymer selectivity, conversion rate, and yield of 1,3-butadiene (BD) when converting ethanol to 1,3-butadiene were determined (all after 1 hour had elapsed from the start of reaction).

Specifically, a reaction bed was formed by filling a stainless-steel cylindrical reaction tube having a diameter of $\frac{1}{2}$ inch (1.27 cm) and a length of 15.7 inches (40 cm) with 3.4 g of the catalyst. Next, the reaction temperature (temperature of the reaction bed) was set to 325° C., and the reaction pressure (pressure of the reaction bed) was set to 0.1 MPa. The raw material was fed into the reaction tube at SV 1200 L/hr/catalyst amount (L-catalyst) to obtain a production gas. The raw material was a mixed gas of 30% by volume ethanol (gas equivalent) and 70% by volume nitrogen (gas equivalent).

The recovered production gas was analyzed by gas chromatography, and the BD selectivity, crotonaldehyde selectivity, conversion rate, and BD yield ([conversion rate]×[BD selectivity]) were determined. In addition, the "conversion rate (raw material conversion rate)" is the percentage of the number of moles consumed among the number of moles of the raw material.

Example 1-1

A beaker was charged with 2 g of P123 ([(HO(CH$_2$CH$_2$O)$_{20}$(CH$_2$CH(CH$_3$)O)$_{70}$(CH$_2$CH$_2$O)$_{20}$)H], manufactured by BASF) as a surfactant, then 65 mL of water and 35 mL of 2 N hydrochloric acid were added, and the mixture was stirred at a speed of 100 rpm under ordinary temperature and pressure conditions to dissolve the surfactant. While stirring the aqueous solution in which the surfactant was dissolved at a rate of 100 rpm under ordinary temperature and pressure conditions, a total of 64 mg of hafnium chloride (HfCl$_4$) was added at a rate of 10 mg/min. After visually confirming that all of the hafnium chloride had dissolved, the mixture was stirred at a rate of 100 rpm under ordinary temperature and pressure conditions, and 4.2 g of tetraethoxysilane was added at a rate of addition of 0.1 g/min to prepare a raw material solution. The concentration of hafnium chloride in the raw material solution was 0.64 g/L, the tetraethoxysilane concentration was 4.8 g/L, and the hydrochloric acid concentration was 0.7 mol/L. Then, a suspension was obtained by leaving the raw material solution to stand for 20 hours at 40° C.

The suspension was left to stand for 20 hours at 100° C., then filtered, and washed with ethanol and water. The powder was then transferred to a petri dish, and dried for 4 hours in an oven kept at a temperature of 110° C. to obtain a solid colloid.

The obtained solid colloid was heated to 550° C. at a rate of temperature increase of 5° C./min in an air atmosphere using an electric furnace, and fired at 550° C. for 5 hours to produce a catalyst, which was a complex oxide including Hf and Si.

Figure 2:
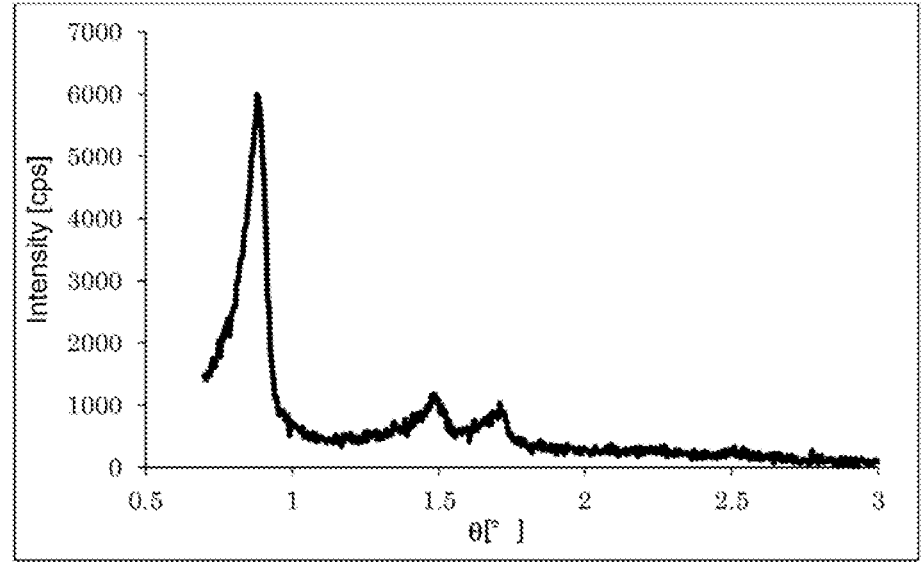
FIG. 2 is an X-ray diffraction chart of the catalyst of Example 1.

The X-ray diffraction lines of the catalyst were measured by the above-described measurement method. As a result, an X-ray diffraction peak was observed at θ=0.90° (half width at half maximum 0.08°), and an intensity at 6453 cps. Further, the X-ray diffraction graph is as shown in FIG. 2.

The above-described reaction evaluation was carried out on the obtained catalyst, and the BD selectivity, conversion rate, and BD yield were determined.

Example 1-2

Catalyst production, X-ray diffraction line measurement, and catalyst evaluation were carried out in the same manner as in Example 1-1, except that the amount of hafnium chloride (HfCl$_4$) used in Example 1-1 was changed to 71 mg. The results are shown in Table 1.

Example 1-3

Catalyst production, X-ray diffraction line measurement, and catalyst evaluation were carried out in the same manner as in Example 1-1, except that the amount of hafnium chloride (HfCl$_4$) used in Example 1-1 was changed to 80 mg. The results are shown in Table 1.

Example 1-4

Catalyst production, X-ray diffraction line measurement, and catalyst evaluation were carried out in the same manner as in Example 1-1, except that the amount of hafnium chloride (HfCl$_4$) used in Example 1-1 was changed to 106 mg. The results are shown in Table 1.

Example 1-5

Catalyst production, X-ray diffraction line measurement, and catalyst evaluation were carried out in the same manner as in Example 1-1, except that the amount of hafnium chloride (HfCl$_4$) used in Example 1-1 was changed to 128 mg. The results are shown in Table 1.

Example 1-6

Catalyst production, X-ray diffraction line measurement, and catalyst evaluation were carried out in the same manner as in Example 1-1, except that the amount of hafnium chloride (HfCl$_4$) used in Example 1-1 was changed to 160 mg. The results are shown in Table 1.

Example 1-7

Catalyst production, X-ray diffraction line measurement, and catalyst evaluation were carried out in the same manner as in Example 1-1, except that the amount of hafnium chloride (HfCl$_4$) used in Example 1-1 was changed to 256 mg. The results are shown in Table 1.

Example 1-8

Catalyst production, X-ray diffraction line measurement, and catalyst evaluation were carried out in the same manner as in Example 1-1, except that the hafnium chloride (HfCl$_1$) used in Example 1-5 was changed to zirconium chloride (ZrCl$_4$). The results are shown in Table 1.

Example 1-9

Catalyst production, X-ray diffraction line measurement, and catalyst evaluation were carried out in the same manner as in Example 1-1, except that the hafnium chloride (HfCl$_4$) used in Example 1-5 was changed to niobium chloride (NbCl$_5$). The results are shown in Table 1.

Example 1-10

Catalyst production, X-ray diffraction line measurement, and catalyst evaluation were carried out in the same manner as in Example 1-1, except that the hafnium chloride (HfCl$_4$) used in Example 1-5 was changed to tantalum chloride (TaCl$_5$). The results are shown in Table 1.

Comparative Example 1-1

Hafnium chloride (HfCl$_4$) was added to a solution obtained by mixing 65 mL of water and 35 mL of 2 N hydrochloric acid, and the mixture was then stirred to dissolve the metal oxide. 4.2 g of tetraethoxysilane was added to the mixture at 0.1 g/min to prepare a raw material solution. Then, a suspension was obtained by stirring the raw material solution for 20 hours at 40° C.

The suspension was aged for 20 hours at 100° C., then filtered, and washed with ethanol and water. The powder was then transferred to a petri dish, and dried in an oven kept at a temperature of 110° C. to obtain a solid colloid.

The obtained solid colloid was fired for 5 hours at 550° C. in an air atmosphere using an electric furnace to produce a catalyst, which was a complex oxide including Hf and Si. X-ray diffraction line measurement, and catalyst evaluation on the catalyst were carried out. The results are shown in Table 1.

Examples Corresponding to Second Invention (Nitrogen Gas Adsorption Measurement Method)

Before performing the measurement, a sample of the catalyst was prepared. About 100 mg of the catalyst was weighed into a mortar, and ground using a pestle to adjust the particle size to 44 μm or less. About 10 mg of the adjusted catalyst was weighed out, and sealed in a sample tube. Each sample tube was heated to 110° C. and vacuum degassed for 10 hours. For the nitrogen gas adsorption measurement, an adsorption and desorption isotherm were measured in a relative pressure range of 0 to 0.98 using a BELSORP-mini specific surface area/pore distribution measuring device manufactured by MicrotrackBell Corp. The specific surface area was calculated by applying the BET

TABLE 1

| | | Catalyst composition | | X-ray diffraction profile of catalyst (low angle range) | | | | |
| | | Molar ratio | Mol % of element X | | | | | |
| | Element X | between element X and Si (—) Si/X | with respect to total of element X and Si X/(Si + X) × 100 | Angle of diffraction peak: θ (°) | Intensity of diffraction peak: I (cps) | Half width at half maximum H of diffraction peak (°) | I/H | |
|---|---|---|---|---|---|---|---|---|
| Example 1-1 | Hf | 100 | 1.0 | 0.90 | 6453 | 0.08 | 80662.5 | |
| Example 1-2 | Hf | 90 | 1.1 | 0.88 | 5980 | 0.05 | 119600.0 | |
| Example 1-3 | Hf | 80 | 1.2 | 0.91 | 4726 | 0.04 | 118150.0 | |
| Example 1-4 | Hf | 60 | 1.6 | 0.85 | 2560 | 0.06 | 42666.7 | |
| Example 1-5 | Hf | 50 | 2.0 | 0.87 | 954 | 0.07 | 13628.6 | |
| Example 1-6 | Hf | 40 | 2.4 | 0.92 | 806 | 0.06 | 13433.3 | |
| Example 1-7 | Hf | 25 | 3.8 | 0.86 | 770 | 0.04 | 19250.0 | |
| Example 1-8 | Zr | 50 | 2.0 | 0.87 | 625 | 0.08 | 7812.5 | |
| Example 1-9 | Nb | 50 | 2.0 | 0.92 | 732 | 0.05 | 14640.0 | |
| Example 1-10 | Ta | 50 | 2.0 | 0.87 | 1034 | 0.08 | 12925.0 | |
| Comparative Example 1-1 | Hf | 100 | 1.0 | — | — | — | — | |

| | Synthesis of diene compound | | | | |
| | Reaction temperature (°) | BD selectivity (%) | Crotonaldehyde selectivity (%) | Conversion rate (%) | BD yield (%) |
|---|---|---|---|---|---|
| Example 1-1 | 325 | 80.6 | 89.6 | 89.6 | 72 |
| Example 1-2 | 325 | 84.2 | 80.9 | 80.9 | 68 |
| Example 1-3 | 325 | 84.6 | 88.1 | 88.1 | 75 |
| Example 1-4 | 325 | 82.9 | 89.1 | 89.1 | 74 |
| Example 1-5 | 325 | 83.3 | 81.3 | 81.3 | 68 |
| Example 1-6 | 325 | 82.4 | 87.7 | 87.7 | 72 |
| Example 1-7 | 325 | 62.5 | 97.3 | 97.3 | 61 |
| Example 1-8 | 325 | 60.9 | 66.8 | 66.8 | 41 |
| Example 1-9 | 325 | 63.1 | 85.1 | 85.1 | 54 |
| Example 1-10 | 325 | 44.6 | 81.9 | 81.9 | 37 |
| Comparative Example 1-1 | 325 | 64.3 | 59.6 | 59.6 | 38 |

From the above results, it can be read from the examples and the comparative example that when one or more peaks are observed at an intensity of 100 csp or more in the range of X-ray diffraction line θ=6° or less, the path for producing butadiene from crotonaldehyde progresses quickly, and there is an effect of improving butadiene selectivity. An effect such as that obtained in the examples is considered to be due to the fact that when mesopores having a regular arrangement are present in the catalyst, the frequency of collisions increases because the ethanol of the raw material and the crotonaldehyde, which is an intermediate product, enter the mesopores more easily, thereby improving reactivity and enabling butadiene to be produced.

method to data in the relative pressure range of 0.05 to 0.25 from the measured adsorption and desorption isotherm. The average pore size was calculated by applying the BJH method to data in the relative pressure range of 0.1 to 0.98 from the measured adsorption and desorption isotherm.

(Catalyst Evaluation: Diene Compound Synthesis)

Using the catalysts prepared in Examples 2-1 to 2-10 and Comparative Examples 2-1 to 2-3, 1,3-butadiene (BD) selectivity, polymer selectivity, conversion rate, and yield of 1,3-butadiene (BD) when converting ethanol to 1,3-butadiene were determined.

Specifically, a reaction bed was formed by filling a stainless-steel cylindrical reaction tube having a diameter of ½ inch (1.27 cm) and a length of 15.7 inches (40 cm) with 3.4 g of the catalyst. Next, the reaction temperature (temperature of the reaction bed) was set to 325° C., and the reaction pressure (pressure of the reaction bed) was set to 0.1 MPa. The raw material was fed into the reaction tube at SV 1200 L/hr/catalyst amount (L-catalyst) to obtain a production gas. The raw material was a mixed gas of 30% by volume ethanol (gas equivalent) and 70% by volume nitrogen (gas equivalent).

The recovered production gas was analyzed by gas chromatography, and the conversion rate, and BD yield ([conversion rate]×[BD selectivity]) one hour and five hours after the reaction started were determined. The "conversion rate (raw material conversion rate)" is the percentage of the number of moles consumed among the number of moles of the raw material.

Example 2-1

A beaker was charged with 2 g of P123 ([(HO(CH$_2$CH$_2$O)$_{20}$(CH$_2$CH(CH$_3$)O)$_{70}$(CH$_2$CH$_2$O)$_{20}$)H], manufactured by BASF) as a surfactant, then 65 mL of water and 35 mL of 2 N hydrochloric acid were added, and the mixture was stirred at a speed of 100 rpm under ordinary temperature and pressure conditions to dissolve the surfactant. While stirring the aqueous solution in which the surfactant was dissolved at a rate of 100 rpm under ordinary temperature and pressure conditions, a total of 64 mg of hafnium chloride (HfCl$_4$) was added at a rate of 10 mg/min. After visually confirming that all of the hafnium chloride had dissolved, the mixture was stirred at a rate of 100 rpm under ordinary temperature and pressure conditions, and 4.2 g of tetraethoxysilane was added at a rate of addition of 1 g/min to prepare a raw material solution. The concentration of hafnium chloride in the raw material solution was 0.64 g/L, the tetraethoxysilane concentration was 4.8 g/L, and the hydrochloric acid concentration was 0.7 mol/L. Then, a suspension was obtained by leaving the raw material solution to stand for 20 hours at 40° C.

The suspension was left to stand for 20 hours at 100° C., then filtered, and washed with ethanol and water. The powder was then transferred to a petri dish, and dried for 4 hours in an oven kept at a temperature of 110° C. to obtain a solid colloid.

The obtained solid colloid was heated to 550° C. at a rate of temperature increase of 5° C./min in an air atmosphere using an electric furnace, and fired at 550° C. for 5 hours to produce a catalyst, which was a complex oxide including Hf and Si.

The above-described nitrogen gas adsorption measurement and reaction evaluation were carried out on the obtained catalyst. The results are shown in Table 2.

Example 2-2

Catalyst production, the above-described nitrogen gas adsorption measurement, and the above-described reaction evaluation were carried out in the same manner as in Example 2-1, except that the amount of hafnium chloride (HfCl$_4$) used in Example 2-1 was changed to 71 mg. The results are shown in Table 2.

Example 2-3

Catalyst production, the above-described nitrogen gas adsorption measurement, and the above-described reaction evaluation were carried out in the same manner as in Example 2-1, except that the amount of hafnium chloride (HfCl$_4$) used in Example 2-1 was changed to 80 mg. The results are shown in Table 2.

Example 2-4

Catalyst production, the above-described nitrogen gas adsorption measurement, and the above-described reaction evaluation were carried out in the same manner as in Example 2-1, except that the amount of hafnium chloride (HfCl$_4$) used in Example 2-1 was changed to 106 mg. The results are shown in Table 2.

Example 2-5

Catalyst production, the above-described nitrogen gas adsorption measurement, and the above-described reaction evaluation were carried out in the same manner as in Example 2-1, except that the amount of hafnium chloride (HfCl$_4$) used in Example 2-1 was changed to 128 mg. The results are shown in Table 2.

Example 2-6

Catalyst production, the above-described nitrogen gas adsorption measurement, and the above-described reaction evaluation were carried out in the same manner as in Example 2-1, except that the amount of hafnium chloride (HfCl$_4$) used in Example 2-1 was changed to 160 mg. The results are shown in Table 2.

Example 2-7

Catalyst production, the above-described nitrogen gas adsorption measurement, and the above-described reaction evaluation were carried out in the same manner as in Example 2-1, except that the amount of hafnium chloride (HfCl$_4$) used in Example 2-1 was changed to 256 mg. The results are shown in Table 2.

Example 2-8

Catalyst production, the above-described nitrogen gas adsorption measurement, and the above-described reaction evaluation were carried out in the same manner as in Example 2-1, except that the hafnium chloride (HfCl$_4$) used in Example 2-5 was changed to zirconium chloride (ZrCl$_4$). The results are shown in Table 2.

Example 2-9

Catalyst production, the above-described nitrogen gas adsorption measurement, and the above-described reaction evaluation were carried out in the same manner as in Example 2-1, except that the hafnium chloride (HfCl$_4$) used in Example 2-5 was changed to niobium chloride (NbCl$_5$). The results are shown in Table 2.

Example 2-10

Catalyst production, the above-described nitrogen gas adsorption measurement, and the above-described reaction evaluation were carried out in the same manner as in Example 2-1, except that the hafnium chloride (HfCl$_4$) used in Example 2-5 was changed to tantalum chloride (TaCl$_5$). The results are shown in Table 2.

Comparative Example 2-1

Hafnium chloride ($HfCl_4$) was added to a solution obtained by mixing 65 mL of water and 35 mL of 2 N hydrochloric acid, and the mixture was then stirred to dissolve the metal oxide. 4.2 g of tetraethoxysilane was added to the mixture at 0.1 g/min to prepare a raw material solution. Then, a suspension was obtained by stirring the raw material solution for 20 hours at 40° C.

The suspension was aged for 20 hours at 100° C., then filtered, and washed with ethanol and water. The powder was then transferred to a petri dish, and dried in an oven kept at a temperature of 110° C. to obtain a solid colloid.

The obtained solid colloid was fired for 5 hours at 550° C. in an air atmosphere using an electric furnace to produce a catalyst, which was a complex oxide including Hf and Si, and the above-described nitrogen gas adsorption measurement and reaction evaluation were carried out. The results are shown in Table 2.

pestle to adjust the particle size to 44 μm or less. The particle size-adjusted catalyst was uniformly filled into holes in a sample filling portion of a sample plate, and adjusted so that the surface of the sample plate and the catalyst surface were in the same plane.

For the X-ray diffraction line measurement, a sample horizontal-type multipurpose X-ray diffraction device Ultima III manufactured by Rigaku Corporation was used. A copper tube made of pure copper was used for the anticathode, and a characteristic X-ray of CuKα (wavelength ($\lambda$)=1.5418 Å (0.15418 nm)) was used for diffraction. The diffraction meter had a divergence slit of ½°, a divergence longitudinal restriction slit of 10 mm, a scattering slit of 2°, and a light receiving slit of 0.15 mm. Then, X-rays were irradiated on the prepared catalyst sample under conditions of a tube voltage of 40 kV and a tube current of 20 mA. The scanning angle of the goniometer was set in the range of 3 to 60°, and the measurement was carried out at a scanning speed of 2°/min.

TABLE 2

| | Catalyst composition | | | | | | | | | |
| | | Molar ratio between element X and Si (—) Si/X | Mol % of element X with respect to total of element X and Si X/(Si + X) × 100 | Average pore size and specific surface area of catalyst | | | Synthesis of diene compound | | | |
| | | | | | | | | After 1 hour | | After 5 hours | |
| | Element X | | | Average pore size (nm) | Specific surface area: S ($m^2/g$) | Reaction temperature (° C.) | Conversion rate (%) | BD yield (%) | Conversion rate (%) | BD yield (%) |
| Example 2-1 | Hf | 100 | 1.0 | 12.5 | 1034 | 325 | 89.6 | 72 | 88.5 | 71 |
| Example 2-2 | Hf | 90 | 1.1 | 12.3 | 839 | 325 | 80.9 | 68 | 80.1 | 68 |
| Example 2-3 | Hf | 80 | 1.2 | 11.6 | 954 | 325 | 88.1 | 75 | 87.6 | 74 |
| Example 2-4 | Hf | 60 | 1.6 | 12.1 | 1054 | 325 | 89.1 | 74 | 88.6 | 73 |
| Example 2-5 | Hf | 50 | 2.0 | 12.6 | 897 | 325 | 81.3 | 68 | 79.9 | 66 |
| Example 2-6 | Hf | 40 | 2.4 | 10.3 | 923 | 325 | 87.7 | 72 | 87 | 71 |
| Example 2-7 | Hf | 25 | 3.8 | 9.5 | 1074 | 325 | 97.3 | 61 | 96.5 | 60 |
| Example 2-8 | Zr | 50 | 2.0 | 9.3 | 723 | 325 | 66.8 | 41 | 66.4 | 41 |
| Example 2-9 | Nb | 50 | 2.0 | 8.9 | 963 | 325 | 85.1 | 54 | 85.2 | 54 |
| Example 2-10 | Ta | 50 | 2.0 | 9.7 | 885 | 325 | 81.9 | 37 | 80.6 | 36 |
| Comparative Example 2-1 | Hf | 100 | 1.0 | 1.3 | 635 | 325 | 59.6 | 38 | 40.7 | 26 |

From the above results, it can be read from the examples and the comparative example that when the specific surface area of the catalyst is in the range of 700 to 1200 $m^2/g$ and the average pore size is 2 to 20 nm, there is the effect that the conversion rate is high from the initial reaction period of the catalyst (after 1 hour) and the conversion rate hardly decreases even after 5 hours. The difference of this effect is considered to be due to the high conversion rate as a result of there being sufficient active points present in the catalyst when the specific surface area is within the above range. Further, when the average pore size is within the above range, it is considered that since the collision frequency of the substrates in the pores is appropriate, only the target reaction progresses, and there is produced an effect in which a deterioration caused by blocking of pore diameters due to the production of polymer products as a result of an excessive progression of reaction does not progress.

Examples Corresponding to Third Invention (X-Ray Diffraction Line Measurement Method)

Before performing X-ray diffraction line measurement, a sample of the catalyst was prepared. First, about 100 mg of the catalyst was weighed into a mortar, and ground using a After the measurement was finished, the obtained data was analyzed. The data was displayed on a graph in Excel or the like with angle on the horizontal axis and cps on the vertical axis, and the presence or absence of a peak was confirmed. When a peak was present, the highest value of cps was taken as the apex of the peak, and the difference between the angle of the apex and the angle of the location indicating the cps value of half of the apex cps value was calculated and taken as the half width at half maximum. When the half width at half maximum is different on the left and right of the peak, the larger value was taken as the half width at half maximum. When there was a plurality of peaks, the half width at half maximum was calculated for each of those peaks. Further, when the peaks overlapped and the half width at half maximum could not be calculated, peak fitting using a least squares method or the like was performed to separate the peaks, and then the half width at half maximum was calculated.

(Catalyst Evaluation: Diene Compound Synthesis)

Using the catalysts prepared in Examples 3-1 to 3-10 and Comparative Examples 3-1 to 3-3, 1,3-butadiene (BD) selectivity, polymer selectivity, conversion rate, and yield of 1,3-butadiene (BD) when converting ethanol to 1,3-butadiene were determined (all after 1 hour had elapsed from the start of reaction).

Specifically, a reaction bed was formed by filling a stainless-steel cylindrical reaction tube having a diameter of ½ inch (1.27 cm) and a length of 15.7 inches (40 cm) with 3.4 g of the catalyst. Next, the reaction temperature (temperature of the reaction bed) was set to 325° C., and the reaction pressure (pressure of the reaction bed) was set to 0.1 MPa. The raw material was fed into the reaction tube at SV 1200 L/hr/catalyst amount (L-catalyst) to obtain a production gas. The raw material was a mixed gas of 30% by volume ethanol (gas equivalent) and 70% by volume nitrogen (gas equivalent).

The recovered production gas was analyzed by gas chromatography, and the BD selectivity, polymer selectivity, conversion rate, and BD yield ([conversion rate]×[BD selectivity]) were determined. The "BD selectivity" is, of the number of moles of the raw material consumed by the reaction using the catalyst, the percentage of the number of moles of the raw material converted to butadiene. The "polymer selectivity" is 100%−([BD selectivity %]+[methane selectivity %]+[ethylene selectivity %]+[diethyl ether selectivity %]+[propene selectivity %]+[propane selectivity %]+[butene selectivity %]+[butane selectivity %]+[acetaldehyde selectivity %]+[ethyl acetate selectivity %]. In addition, the "conversion rate (raw material conversion rate)" is the percentage of the number of moles consumed among the number of moles of the raw material.

Example 3-1

A beaker was charged with 2 g of P123 ([(HO(CH$_2$CH$_2$O)$_{20}$(CH$_2$CH(CH$_3$)O)$_{70}$(CH$_2$CH$_2$O)$_{20}$)H], manufactured by BASF) as a surfactant, then 65 mL of water and 35 mL of 2 N hydrochloric acid were added, and the mixture was stirred at a speed of 100 rpm under ordinary temperature and pressure conditions to dissolve the surfactant. While stirring the aqueous solution in which the surfactant was dissolved at a rate of 100 rpm under ordinary temperature and pressure conditions, a total of 64 mg of hafnium chloride (HfCl$_4$) was added at a rate of 10 mg/min. After visually confirming that all of the hafnium chloride had dissolved, the mixture was stirred at a rate of 100 rpm under ordinary temperature and pressure conditions, and 4.2 g of tetraethoxysilane was added at a rate of addition of 1 g/min to prepare a raw material solution. The concentration of hafnium chloride in the raw material solution was 0.64 g/L, the tetraethoxysilane concentration was 4.8 g/L, and the hydrochloric acid concentration was 0.7 mol/L. Then, a suspension was obtained by leaving the raw material solution to stand for 20 hours at 40° C.

The suspension was left to stand for 20 hours at 100° C., then filtered, and washed with ethanol and water. The powder was then transferred to a petri dish, and dried for 4 hours in an oven kept at a temperature of 110° C. to obtain a solid colloid.

The obtained solid colloid was heated to 550° C. at a rate of temperature increase of 5° C./min in an air atmosphere using an electric furnace, and fired at 550° C. for 5 hours to produce a catalyst, which was a complex oxide including Hf and Si.

Figure 3:
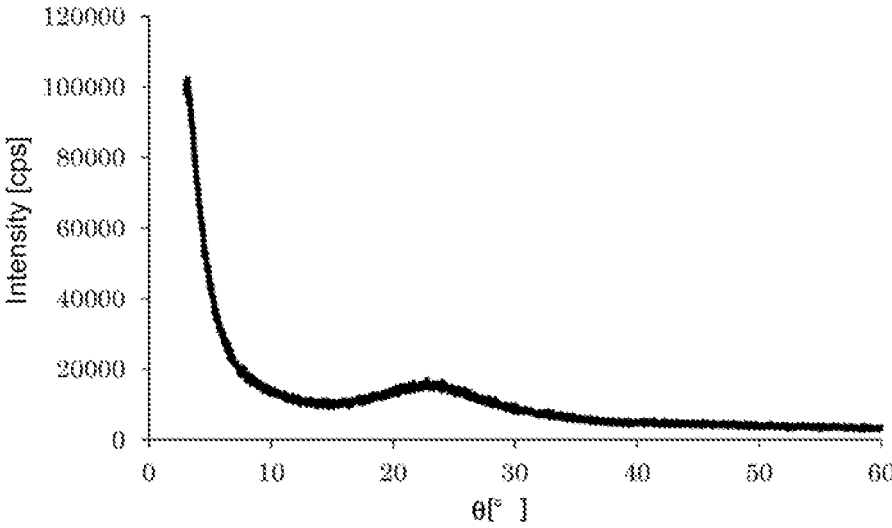
FIG. 3 is an X-ray diffraction chart of the catalyst of Example 3-1.

The X-ray diffraction lines of the catalyst were measured by the above-described measurement method. As a result, an X-ray diffraction peak was observed at θ=22.8° (half width at half maximum 7.8°), and an intensity at 16916 cps. Further, the X-ray diffraction graph is as shown in FIG. 3.

The above-described reaction evaluation was carried out on the obtained catalyst, and the BD selectivity, conversion rate, and BD yield were determined. The results are shown in Table 3.

Example 3-2

Catalyst production, X-ray diffraction line measurement, and catalyst evaluation were carried out in the same manner as in Example 3-1, except that the amount of hafnium chloride (HfCl$_4$) used in Example 3-1 was changed to 71 mg. The results are shown in Table 3.

Example 3-3

Catalyst production, X-ray diffraction line measurement, and catalyst evaluation were carried out in the same manner as in Example 3-1, except that the amount of hafnium chloride (HfCl$_4$) used in Example 3-1 was changed to 80 mg. The results are shown in Table 3.

Example 3-4

Catalyst production, X-ray diffraction line measurement, and catalyst evaluation were carried out in the same manner as in Example 3-1, except that the amount of hafnium chloride (HfCl$_4$) used in Example 3-1 was changed to 106 mg. The results are shown in Table 3.

Example 3-5

Catalyst production, X-ray diffraction line measurement, and catalyst evaluation were carried out in the same manner as in Example 3-1, except that the amount of hafnium chloride (HfCl$_4$) used in Example 3-1 was changed to 128 mg. The results are shown in Table 3.

Example 3-6

Catalyst production, X-ray diffraction line measurement, and catalyst evaluation were carried out in the same manner as in Example 3-1, except that the amount of hafnium chloride (HfCl$_4$) used in Example 3-1 was changed to 160 mg. The results are shown in Table 3.

Example 3-7

Catalyst production, X-ray diffraction line measurement, and catalyst evaluation were carried out in the same manner as in Example 3-1, except that the amount of hafnium chloride (HfCl$_4$) used in Example 3-1 was changed to 256 mg. The results are shown in Table 3.

Example 3-8

Catalyst production, X-ray diffraction line measurement, and catalyst evaluation were carried out in the same manner as in Example 3-1, except that the hafnium chloride (HfCl$_4$) used in Example 3-5 was changed to zirconium chloride (ZrCl$_4$). The results are shown in Table 3.

Example 3-9

Catalyst production, X-ray diffraction line measurement, and catalyst evaluation were carried out in the same manner as in Example 3-1, except that the hafnium chloride (HfCl$_4$)

used in Example 3-5 was changed to niobium chloride (NbCl$_5$). The results are shown in Table 3.

Example 3-10

Catalyst production, X-ray diffraction line measurement, and catalyst evaluation were carried out in the same manner as in Example 3-1, except that the hafnium chloride (HfCl$_4$) used in Example 3-5 was changed to tantalum chloride (TaCl$_5$). The results are shown in Table 3.

Comparative Example 3-1

64 mg of hafnium chloride (HfCl$_4$) was dissolved in water to form an impregnation solution. The impregnation solution was added dropwise onto a porous carrier (silica, particle size: 1.18 to 2.36 mm, average pore size: 10 nm, total pore volume: 1.01 mL/g, specific surface area: 283 m$^2$/g). This porous body was dried at 110° C. for 3 hours, and then fired at 400° C. for 4.5 hours to produce a catalyst. X-ray diffraction line measurement and catalyst evaluation were performed. The results are shown in Table 3.

Comparative Example 3-2

Catalyst production, X-ray diffraction line measurement, and catalyst evaluation were carried out in the same manner as in Comparative Example 1, except that the amount of the hafnium chloride (HfCl$_4$) used in Comparative Example 3-1 was changed to 256 mg. The results are shown in Table 3.

TABLE 3

| | | Catalyst composition | | X-ray diffraction profile of catalyst (high angle range) | | | |
|---|---|---|---|---|---|---|---|
| | Element X | Molar ratio between element X and Si (—) Si/X | Mol % of element X with respect to total of element X and Si X/(Si + X) × 100 | Angle of diffraction peak: θ (°) | Intensity of diffraction peak: I (cps) | Half width at half maximum H of diffraction peak (°) | I/H |
| Example 3-1 | Hf | 100 | 1.0 | 22.8 | 16916 | 7.8 | 2168.7 |
| Example 3-2 | Hf | 90 | 1.1 | 22.8 | 17050 | 7.4 | 2304.1 |
| Example 3-3 | Hf | 80 | 1.2 | 22.9 | 12733 | 8.7 | 1463.6 |
| Example 3-4 | Hf | 60 | 1.6 | 23.5 | 11050 | 8.1 | 1364.2 |
| Example 3-5 | Hf | 50 | 2.0 | 24.2 | 12074 | 8.7 | 1387.8 |
| Example 3-6 | Hf | 40 | 2.4 | 22.9 | 13516 | 8.6 | 1571.6 |
| Example 3-7 | Hf | 25 | 3.8 | 23.9 | 22633 | 10.4 | 2176.3 |
| Example 3-8 | Zr | 50 | 2.0 | 24.2 | 15840 | 8.4 | 1885.7 |
| Example 3-9 | Nb | 50 | 2.0 | 24.3 | 16384 | 9 | 1820.4 |
| Example 3-10 | Ta | 50 | 2.0 | 24.4 | 17468 | 8.6 | 2031.2 |
| Comparative Example 3-1 | Hf | 100 | 1.0 | 28.2 | 192183 | 0.64 | 300285.9 |
| Comparative Example 3-2 | Hf | 25 | 3.8 | 28.6 | 50192 | 0.51 | 98415.7 |

| | Synthesis of diene compound | | | | |
|---|---|---|---|---|---|
| | Reaction temperature (° C.) | BD selectivity (%) | Polymer selectivity (%) | Conversion rate (%) | BD yield (%) |
| Example 3-1 | 325 | 80.6 | 4.9 | 89.6 | 72 |
| Example 3-2 | 325 | 84.2 | 0.4 | 80.9 | 68 |
| Example 3-3 | 325 | 84.6 | 2.3 | 88.1 | 75 |
| Example 3-4 | 325 | 82.9 | 4.5 | 89.1 | 74 |
| Example 3-5 | 325 | 83.3 | 1.5 | 81.3 | 68 |
| Example 3-6 | 325 | 82.4 | 1.5 | 87.7 | 72 |
| Example 3-7 | 325 | 62.5 | 0.7 | 97.3 | 61 |
| Example 3-8 | 325 | 60.9 | 1.5 | 66.8 | 41 |
| Example 3-9 | 325 | 63.1 | 3.9 | 85.1 | 54 |
| Example 3-10 | 325 | 44.6 | 2.6 | 81.9 | 37 |
| Comparative Example 3-1 | 325 | 59.1 | 33.5 | 64.4 | 38 |
| Comparative Example 3-2 | 325 | 55.8 | 34.9 | 52.7 | 29 |

From the above results, it can be confirmed that when a peak having a half width at half maximum of 1° or more is observed in the X-ray diffraction line range θ=10 to 40°, there is an effect in that the amount of polymer having a larger molecular weight than butadiene produced as a result of excessive progression of reaction decreases, and butadiene selectivity is improved. The difference of this effect is considered to be that hafnium, which is the reaction site of the catalyst, is not present as an agglomeration of hafnium oxide alone, but is dispersed in the catalyst as a complex oxide with silica, so that the surface area per reaction site is reduced and the progression of excessive progression of reaction can be suppressed.

REFERENCE SIGNS LIST 1 reaction tube
2 reaction bed
3 feed tube
4 discharge tube
5 temperature control unit
6 pressure control unit
10 butadiene production apparatus
The invention claimed is:

1. A catalyst comprising:
at least one element X selected from the group consisting of Hf, Zr, and Nb; and
at least one element Z selected from the group consisting of Group 14 elements, wherein
at least one diffraction peak is observed in a low angle range of θ=6° or less in an X-ray diffraction profile observed using X-ray diffraction,
the at least one diffraction peak has a ratio (I/H) of a peak intensity I to a half width at half maximum H of the diffraction peak of 5000 or more,
no diffraction peak due to a single oxide of the element X is observed in a high-angle range of θ=10° to 40° in the X-ray diffraction profile observed using X-ray diffraction, and a molar content (X/(X+Z)×100) of the element X with respect to the total amount (mole) of the element X and the element Z is 0.5 to 6 mol %.

2. The catalyst according to claim 1, wherein the element X is Hf and the element Z is Si.

3. The catalyst according to claim 1, wherein the catalyst is a diene compound synthesis catalyst for synthesizing a diene compound from a raw material including an alcohol.

4. The catalyst according to claim 3, wherein the raw material includes ethanol and/or acetaldehyde.

5. The catalyst according to claim 1, wherein a BET specific surface area is 700 to 1200 m²/g and an average pore size is 2 to 20 nm.

6. The catalyst according to claim 1, wherein at least one diffraction peak having a half width at half maximum of 1° or more is observed in a high angle range of θ=10° to 40° in an X-ray diffraction profile observed using X-ray diffraction.

7. A method for producing a diene compound, comprising contacting a raw material including an alcohol with the catalyst according to claim 1 to produce the diene compound.

8. A method for producing a polymer, comprising producing the polymer by using at least a portion of the diene compound produced by the method for producing a diene compound according to claim 7 as a polymer raw material.

9. A method for producing a polymer formed article, comprising forming the polymer produced by the method for producing a polymer according to claim 8.

10. The catalyst according to claim 1, wherein in the X-ray diffraction profile observed using X-ray diffraction, at least one diffraction peak due to a complex oxide including the element X and an element Y, having a half-width at half maximum of 1° or more, is observed in the high-angle range of θ=10° to 40°.

* * * * *